United States Patent [19]
Potter

[11] Patent Number: 5,399,350
[45] Date of Patent: Mar. 21, 1995

[54] PROTEINACEOUS OIL SPILL DISPERSANT
[75] Inventor: Richard Potter, Seeley Lake, Mont.
[73] Assignee: Nurture, Inc., Missoula, Mont.
[21] Appl. No.: 27,861
[22] Filed: Mar. 8, 1993

Related U.S. Application Data
[63] Continuation-in-part of Ser. No. 505,126, Apr. 5, 1990.
[51] Int. Cl.$^6$ .................. A01N 25/26; A01N 25/28; A23B 4/03; A23B 4/044
[52] U.S. Cl. .................... 424/418; 426/464; 426/467; 514/937; 514/951
[58] Field of Search ............... 424/418, 499; 514/937, 514/951; 426/464, 467

[56] References Cited

U.S. PATENT DOCUMENTS

| | | | |
|---|---|---|---|
| 1,787,585 | 1/1931 | McBeth et al. | 514/773 |
| 1,890,860 | 12/1932 | Omohundro | 514/653 |
| 1,920,926 | 8/1933 | Noonan | 514/762 |
| 2,355,029 | 8/1944 | Musher et al. | 252/1 |
| 2,436,818 | 5/1945 | Musher | 424/49 |
| 2,754,215 | 7/1956 | Evans et al. | 426/96 |
| 2,876,164 | 3/1959 | Wershaw | 514/772.5 |
| 3,069,361 | 12/1962 | Cogswell | 252/363 |
| 3,394,119 | 7/1968 | Luce et al. | 530/334 |
| 3,609,096 | 9/1971 | Salomone | 252/352 |
| 3,676,357 | 7/1972 | Ciuti et al. | 502/402 |
| 3,714,063 | 1/1973 | Salomone | 252/312 |
| 3,755,560 | 8/1973 | Dickert et al. | 514/772.6 |
| 3,793,218 | 2/1974 | Canevari | 252/312 |
| 3,843,517 | 10/1974 | McKinney et al. | 210/611 |
| 3,900,421 | 8/1975 | Fusey | 252/312 |
| 4,014,995 | 3/1977 | Juliano et al. | 514/783 |
| 4,098,694 | 7/1978 | Perlaky | 252/312 |
| 4,110,213 | 8/1978 | Tennant et al. | 210/780 |
| 4,217,370 | 8/1980 | Rawlings et al. | 426/98 |
| 4,218,482 | 8/1980 | Cook et al. | 426/72 |
| 4,224,152 | 9/1980 | Lepain | 210/729 |
| 4,238,509 | 12/1980 | Evans et al. | 514/777 |
| 4,246,257 | 1/1981 | Elliot et al. | 424/78.03 |
| 4,248,733 | 2/1981 | States, Sr. | 252/355 |
| 4,341,799 | 7/1982 | Good | 514/784 |
| 4,382,873 | 5/1983 | Gatellier et al. | 252/312 |
| 4,462,910 | 7/1984 | Lepain et al. | 210/610 |
| 4,469,603 | 9/1984 | Lepain et al. | 210/749 |
| 4,483,716 | 11/1984 | Heller | 134/7 |
| 4,560,482 | 12/1985 | Canevari | 210/749 |
| 4,597,893 | 7/1986 | Byford et al. | 252/354 |
| 4,623,468 | 11/1986 | Lepain et al. | 210/749 |
| 4,677,065 | 6/1987 | Buchbjerg et al. | 435/68.1 |
| 4,734,287 | 3/1988 | Singer et al. | 426/41 |
| 4,764,285 | 8/1988 | Robbins et al. | 210/749 |
| 4,826,818 | 5/1989 | Mori et al. | 514/21 |
| 4,830,759 | 5/1989 | Charlier | 210/749 |
| 4,855,156 | 8/1989 | Singer et al. | 426/565 |
| 4,978,459 | 12/1990 | Bock et al. | 210/749 |
| 5,023,080 | 6/1991 | Gupta | 424/405 |
| 5,051,192 | 9/1991 | Charlier | 210/749 |
| 5,082,563 | 1/1992 | Webb et al. | 210/631 |
| 5,112,495 | 5/1992 | Bartha et al. | 210/691 |

FOREIGN PATENT DOCUMENTS

| | | |
|---|---|---|
| 0146174 | 6/1985 | European Pat. Off. |
| 0740217 | 10/1968 | France |
| 2287214 | 5/1976 | France |
| 2571253 | 4/1986 | France |
| 0017387 | 2/1975 | Japan |
| 56-015203 | 2/1981 | Japan |
| 57-074384 | 5/1982 | Japan |

OTHER PUBLICATIONS

Coe and Juliano, "A New Natural Ingredient for Cosmetic Formulators", *DC&I*, pp. 48–56 (Sep. 1973).
Food Chemistry, 2d Ed. (Fennema), Marcel Dekkar, Inc. (1985), pp. 298–303.
Fuller, H. I. (1971), "The use of floating absorbents and gelling techniques for combating oil spills on water", J. Inst. of Petroleum 57:35–43.

*Primary Examiner*—Thurman K. Page
*Assistant Examiner*—Carlos Azpuru
*Attorney, Agent, or Firm*—Knobbe, Martens, Olson & Bear

[57] ABSTRACT

The present invention relates to a substantially intact proteinaceous particulate material that is effective as an oil spill dispersant composition. In a preferred respect, the invention is a grain product (such as oats) from which lipids are removed through organic solvent extraction. When such compositions are applied to an oil spill, they will adsorb oil, emulsify it, and finally disperse the oil with high efficiency. Moreover, the compositions are substantially non-toxic.

26 Claims, 20 Drawing Sheets

NOTE: 100-300µ E GRADE PARTICLE SIZE DISTRIBUTION;
23 C; FRESH OIL, y=349x=25, R**2=0.976;
WEATHERED OIL, y=342.5x-19.8, R**2=0.76;

PROTEINACEOUS OIL SPILL DISPERSANT

RELATED APPLICATIONS

This application is a continuation in part of U.S. application Ser. No. 07/505,126, filed Apr. 5, 1990, the contents of which are hereby incorporated by reference.

BACKGROUND OF THE INVENTION

1. Field of the Invention

The present invention is related to the use of a natural proteinaceous material that acts as an oil dispersant, in particular an oat protein from which free lipids are removed that emulsifies and disperses oil spills.

2. Background of the Prior Art

When an oil spill occurs, the most desirable remedy is to recover the spilled oil. However, rarely is more than 10% of the oil released in a major spill ultimately recovered. Oil that cannot be recovered may be dispersed, thus protecting shorelines, preventing the oiling of marine birds and mammals, and speeding biodegradation of the oil. One reason why oil dispersal has not been widely used is that dispersants, by and large, are quite toxic.

Furthermore, there is reason to believe that the effectiveness of a surfactant-based dispersant is in direct correlation with its toxicity. A surfactant at a concentration sufficient to emulsify petroleum may also be expected to have a variety of ill effects on marine organisms including tissue irritation, changes in gill membrane permeability that bring on asphyxiation, and increase in uptake of foreign chemicals.

Commercially available oil dispersants are all liquids and possess relatively high $LD_{50}$'s. These include Corexit® 9527 (Exxon), a surfactant-solvent product for oil dispersal; Naxchem® Dispersant K (formerly known as Conco Dispersant K and now sold by Ruetgers-Nease), a product consisting primarily of surfactants and alcohols; Atlant'ol® AT-7 (Aspra, Inc.), a water-based product; Omni-Clean® OSD (Delta Omega Technologies), a water-based product containing synthetic surfactants and fatty acid soaps and marketed as a safe, low-toxicity product; Corexit 9550 (Exxon); and Corexit 7664 (Exxon), a product formerly marketed as an open-sea dispersant but now sold mostly as a beach cleaner.

Surfactants added to oil slicks on water tend to be immediately diluted by the water. Only when sufficient surfactant concentration is present in contact with both water and oil will dispersal occur. Once the surfactant has solubilized the oil, the dispersed droplets mix with greater and greater quantities of water. While this is the desired effect of dispersal, it also tends to dilute the surfactant concentration further, so that resurfacing of oil slicks may occur.

Accordingly, there is a need in the art for an oil spill dispersant that is capable of low energy emulsification of oil spills on water, together with low toxicity.

SUMMARY OF THE INVENTION

We have discovered that a natural protein material (described herein as the "Proteinaceous Dispersant") disperses spilled oil with performance comparable to conventional detergent-type dispersants. However, the Proteinaceous Dispersant of the present invention is particulate. Thus, unlike liquid dispersants, oil associated with a particle in accordance with the present invention is not subject to the emulsion-breaking effects of dilution after dispersal occurs. Similarly, because of this particulate nature, the dispersant of the present invention can be used without suffering deleterious pre-dispersal dilution.

In accordance with one aspect of the present invention, there is provided a method for dispersing an oil spill on water that comprises contacting the spill with a substantially chemically intact proteinaceous particulate material prepared from or derived from seeds, that when applied to oil on top of water disperses a substantial quantity of the oil through forming an oil-in-water emulsion. The seeds in a preferred embodiment are selected from the group consisting of legumes and grains, such as canola, beans, oats, barley, rape seed, and soya. In a highly preferred embodiment, the seeds are oats.

The proteinaceous material may advantageously be obtained by grinding a seed storage protein starting material and extracting the free lipids from the resulting particulate material, preferably with an organic solvent. In preferred embodiments, the proteinaceous materials have a protein concentration of from about 10% to 50%, or more preferably in the range of from about 20% to 30%. Also, in preferred embodiments, the proteinaceous materials have an average particle size of from about 1 $\mu$m to 600 $\mu$m, or more preferably from about 100 $\mu$m to 300 $\mu$m. In a particularly preferred embodiment, the proteinaceous material is derived from oats and has a protein concentration of from about 20% to 30% and an average particle size of from about 100 $\mu$m to 300 $\mu$m. Most preferably, the extraction is completed in a nonaqueous environment at a temperature below about 70 degrees C., preferably below about 45 degrees C.

The proteinaceous materials may optionally be formed into a foam, or another solid shape. Foams can be made, for example, by contacting the proteinaceous material with an organic solvent or other blowing agent, with or without a binder. Preferred binders are selected from the group consisting of salts of magnesium, zinc, or calcium.

The invention also includes a method for cleaning animals, beaches, or properties that are contaminated by oil from an oil spill, comprising applying an effective amount of the Proteinaceous Dispersants of the present invention, working the composition around, over, and into the surface of the contaminated animal, beach, or property, followed by rinsing to remove the oil.

In accordance with yet another embodiment of the present invention, there is provided a oil dispersant composition, that comprises a natural proteinaceous particulate material obtained from seeds and having a protein concentration of from about 10% to about 50% and an average particle size of from about 1 $\mu$m to about 600 $\mu$m, from which lipids have been removed, that when applied to oil on top of water disperses a substantial quantity of the oil through forming an oil-in-water emulsion. In a preferred embodiment, the composition is derived from a proteinaceous starting material that is selected from the group consisting of legumes and grains, such as canola, beans, oats, barley, rape seed, and soya. In a highly preferred embodiment, the seeds are oats.

In still another aspect of the present invention, there is provided an oil dispersant composition, comprising a proteinaceous particulate material formed into a shaped macroscopic particle with a binder or a filler. Moreover, the shaped particles may optionally be coated with a material that is insoluble in water but soluble in oil. Furthermore, the proteinaceous materials, either in powder or shaped form, may also be mixed with an active culture of a bacterium that biodegrades oil.

In preferred embodiments, the proteinaceous materials have a protein concentration of from about 10% to 50%, or more preferably in the range of from about 20% to 30%. Also, in preferred embodiments, the proteinaceous materials have an average particle size of from about 1 μm to 600 μm, or more preferably from about 100 μm to 300 μm. In a particularly preferred embodiment, the proteinaceous material is derived from oats and has a protein concentration of from about 20% to 30% and an average particle size of from about 100 μm to 300 μm.

BRIEF DESCRIPTIONS OF THE FIGURES

FIG. 1 is a chart showing the dispersion efficiencies of various grades of the Proteinaceous Dispersants of the present invention against North Slope Crude Oil in synthetic seawater, as a function of dispersant:oil ratio.

FIG. 2. is a chart showing the dispersion efficiencies of various grades of the Proteinaceous Dispersants of the present invention against No. 6 Fuel Oil in synthetic seawater, as a function of dispersant:oil ratio.

FIG. 3. is a chart showing the dispersion efficiency of the E Grade Proteinaceous Dispersant of the present invention against fresh and weathered North Slope Crude Oil in synthetic seawater, as a function of dispersant:oil ratio.

FIG. 4. is a chart showing the dispersion efficiency of the C Grade Proteinaceous Dispersant of the present invention against No. 6 Fuel Oil in synthetic seawater, as a function of dispersant:oil ratio.

FIG. 5. is a chart showing the dispersion efficiency of the E Grade Proteinaceous Dispersant of the present invention against fresh and weathered Rangely Crude Oil in synthetic seawater, as a function of dispersant:oil ratio.

FIG. 6. is a chart showing the dispersion efficiency of the E Grade Proteinaceous Dispersant of the present invention against fresh and weathered Brent Crude Oil in synthetic seawater, as a function of dispersant:oil ratio.

FIG. 7. is a chart showing the dispersion efficiency of the E Grade Proteinaceous Dispersant of the present invention against a Mousse, formed from 40% North Slope Crude Oil and 60% seawater, as a function of dispersant:oil ratio.

FIG. 8. is a chart showing the effect of temperature on the dispersal efficiency of the E Grade Proteinaceous Dispersant of the present invention against North Slope Crude Oil in synthetic seawater, as a function of dispersant:oil ratio.

FIG. 9. is a chart showing the dispersal efficiency of Corexit ® 9527 against North Slope Crude Oil and No. 6 Fuel Oil in synthetic seawater, as a function of dispersant:oil ratio.

FIG. 10. is a chart showing the dispersal efficiency of Omni-Clean ® OSD against North Slope Crude Oil and No. 6 Fuel Oil in synthetic seawater, as a function of dispersant:oil ratio.

FIG. 11. is a chart showing the dispersal efficiency of Naxchem ® Dispersant K against North Slope Crude Oil and No. 6 Fuel Oil in synthetic seawater, as a function of dispersant:oil ratio.

FIG. 12. is a chart showing the dispersal efficiency of Atlant'ol ® AT-7 against North Slope Crude Oil and No. 6 Fuel Oil in synthetic seawater, as a function of dispersant:oil ratio.

FIG. 13. is a chart showing the dispersal efficiency of Corexit ® 9550 against North Slope Crude Oil and No. 6 Fuel Oil in synthetic seawater, as a function of dispersant:oil ratio.

FIG. 14. is a chart showing the dispersal efficiency of Corexit ® 7664 against North Slope Crude Oil and No. 6 Fuel Oil in synthetic seawater, as a function of dispersant:oil ratio.

FIG. 15. is a gas chromatogram of oil extracted from an abiotic control containing crude oil and sterile synthetic seawater (attenuation setting=64).

FIG. 16. is a gas chromatogram of oil extracted from a sample containing crude oil, bacteria, and sterile synthetic seawater (attenuation setting=64).

FIG. 17. is a gas chromatogram of oil extracted from a sample containing crude oil, bacteria, mineral fertilizer, and sterile synthetic seawater (attenuation setting=64).

FIG. 18. is a gas chromatogram of oil extracted from a sample containing crude oil, bacteria, the E Grade Proteinaceous Dispersant (sterile), and sterile synthetic seawater (attenuation setting=64).

FIG. 19. is a gas chromatogram of oil extracted from a sample containing crude oil, bacteria, the E Grade Proteinaceous Dispersant (unsterile), and sterile synthetic seawater (attenuation setting=64).

FIG. 20. is a gas chromatogram of unweathered North Slope Crude Oil (attenuation setting=128).

DETAILED DESCRIPTION OF THE INVENTION

I. The Proteinaceous Starting Material

Figure 1:
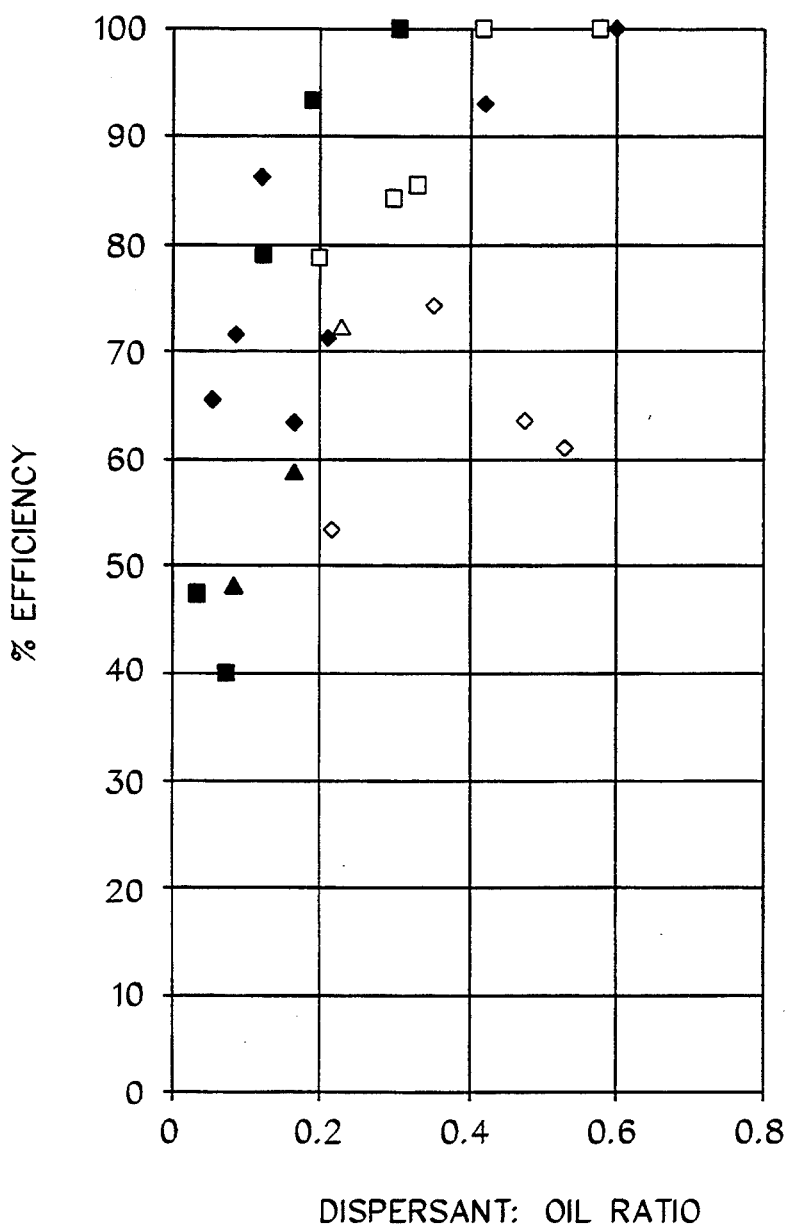
Figure 1:
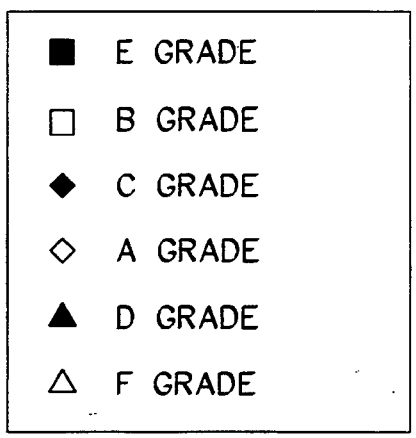

Various processes can be used to prepare the Proteinaceous Dispersant of the present invention from seed-type starting materials.

Oughton, in U.S. Pat. No. 4,154,728, describes a process for separating fractions of differing compositions from comminuted proteinaceous material from a variety of food sources, including wheat, rye, barley, triticale, peas, and buckwheat. The Oughton process comprises mixing the proteinaceous material with an aliphatic hydrocarbon or alcohol suitable to dissolve the lipids in the material. The wet slurry is distributed by means of centrifugation into fractions which differ primarily in protein composition, as well as starch composition. A similar process is applied to comminuted oats in U.S. Pat. Nos. 4,211,695 and 4,211,801, also to Oughton.

To facilitate recovery of the protein, in particular, from the slurry produced in accordance with the foregoing processes, U.S. Pat. Nos. 4,208,295 and 4,208,260 to Oughton disclose the application of an electric field to the mixture in collection of a comminuted oat fraction which clings to the anode. An improved method of recovery is disclosed in U.S. Pat. No. 4,407,841 to Boocock, comprising the addition of aqueous ethanol to the slurry to agglomerate the proteinaceous material and to facilitate the separation thereof.

It is preferred that the proteinaceous materials of the present invention be prepared in a non-aqueous environment, and that the extraction be conducted with a nonpolar solvent, such as hexane. If water is used in the process, some changes in the protein occur. These changes may be at least partially reversed by freeze drying (lyophilization) of the product. Heat is also deleterious, resulting in permanent changes in the properties of the Proteinaceous Dispersant. The process temperature is preferably less than about 70 or 60 degrees C., preferably below about 50 or 40 degrees C., and most preferably below about 35 or even 30 degrees C.

Accordingly, the method of separation of proteins from protein containing materials comprises extracting the oil from the seed with organic solvents, such as propanol, ethanol, or hexanes. This process removes the lipids and allows separation of other insoluble materials. It is preferred to use solvents that are nontoxic, since the materials are intended to be released into the environment and residual solvent may be trapped within the particles.

After the extraction of lipids and separation of the proteinaceous materials, the particles are separated to a desired particle size or range of sizes, depending upon the desired end use of the material. Suitable average particle sizes of the protein compositions that form the Proteinaceous Dispersants of the present invention may be in the range from 1 μm to 600 μm. Preferably, the average particle sizes are from 100 μm to 300 μm.

Subsequent milling and/or separation steps are often unnecessary after extraction of the lipids and other undesired materials. When the proteinaceous dispersant materials are derived from natural seeds, such as grains and legumes, the particles will be irregular in shape due to crushing and fragmenting during the milling process. However, median particle size can be determined by milling parameters or by using a series of graduated sieves or by particle size analysis. Furthermore, in applications requiring more exacting control over the particle sizes, more advanced particle sizing apparatus and methods are available to those of skill in the art, such as gravimetric analyses or digital imagery sizing.

Many suitable protein concentrates or protein particulates are commercially available. For example, soya protein concentrate is available in 92% pure form from Protein Technologies International, St. Louis, Mo., U.S.A. Pea protein concentrates are available from Woodstone Foods, Winnipeg, Canada.

The protein particulates are advantageously dried prior to use to remove solvent and other indigenous volatiles. In addition, depending upon the protein separation process, residual solvent could reside in the interstices of the particulate which could react adversely with other additives.

Drying can be accomplished by any number of known techniques, such as fluid bed drying or subjecting the powder to a vacuum with or without the addition of heat. Often, however, in the case of the Proteinaceous Dispersant compositions of the present invention, sufficient drying may be accomplished through air drying.

II. Oil Dispersant Properties of the Proteinaceous Dispersant Materials

The proteinaceous materials of the present invention are capable of use in conjunction with the clean-up and/or control of spills or release of unwanted or dangerous agents into the environment, including the clean-up and control of oil spills.

The proteinaceous material may be introduced to an area of oil release upon a body of water. Thereafter, the proteinaceous material sorbs the oil, emulsifying or dispersing the oil and producing a fine emulsion that is more easily assimilated into the environment. This method of providing a colloidal dispersion of oil is particularly efficacious, since microbial degradation of the oil can more easily occur.

In order to facilitate maximum contact between the Proteinaceous Dispersant and the oil, dispersant may be prepared in buoyant form. This may be done by adding water to the particulate dispersant, and freeze drying the resulting material. Blowing agents of conventional type may be used. When this material is added to an oil slick, the protein particulate immediately sorbs a large amount of oil. The protein particulate soon begins to break up. The particles which separate form a fine dispersion in the water. The oil appears to be fully entrapped or adsorbed by the particles, even in dispersion, as no subsequent separation of oil and dispersant is observed.

The Proteinaceous Dispersants of the present invention have the ability to adsorb several times their weight of a wide range of substances, including hydrophobic materials such as oils. In addition, these dispersants can function as effective emulsifiers, forming stable emulsions with low-energy mixing. The combination of these two properties makes the Proteinaceous Dispersants effective dispersants for spilled oil. When placed on an oil slick, the Proteinaceous Dispersant particles first adsorb oil, forming an in situ emulsifiable concentrate. Subsequent wave, wind, and current action without further human interaction will create an emulsion that acts to disperse the oil into the water column. Thus, the Proteinaceous Dispersants appear to offer a new and radically different solution to the problem of dispersing spilled oil. Moreover, they do so without adding large additional amounts of toxic materials to the ecosystem.

In fact, the Proteinaceous Dispersant of the present invention, in a preferred embodiment, is an edible cereal grain product, and in past toxicity studies it was found to be essentially harmless to all species on which it was tested. The mechanism by which the Proteinaceous Dispersants disperse oil is not a surfactant mechanism based on micelle formation. Instead, the protein in the compositions appears to bind oil at hydrophobic sites, forming a particle-associated emulsifiable concentrate. This concentrate then disperses in water, forming an emulsion. This emulsion is fundamentally different from one based on surfactants in that the oil-associated Proteinaceous Dispersant particles are incapable of crossing gill membranes or causing other toxic effects associated with surfactants.

It will be appreciated that the Proteinaceous Dispersants may either be administered as a powder to the surface of the water containing the oil, or they may be formed into readily-dispersible solid forms, such as foams, tablets, agglomerates, granules, or pellets (a far more convenient mode of storage and application). Principally, however, whatever mode of administration that is chosen, it is preferred that the Proteinaceous Dispersants are buoyant and float freely upon the upper layer of oil. To achieve these objectives, a variety of production techniques can be used that are well known in the art, such as lyophilization; forming of pellets containing a blowing agent (i.e., hexane), followed by evaporation of the hexane with resulting formation of a foamed, low-density solid; and binding the Proteinaceous Dispersant with a variety of binders, fillers, or excipients. Preferred binders include salts of magnesium, calcium, or zinc, such as stearates in a preferred embodiment. Typically, it is preferred that binders be present in a range of from 0.1 to 0.5 w/w ratio with the Proteinaceous Dispersant.

Moreover, it will be appreciated that pellets can optionally be coated or encapsulated in a material that is insoluble in water, but is soluble in oil, allowing the pellets to become activated only upon contacting the oil spill, for example, an oil soluble varnish. It will also be appreciated that one can incorporate a culture of bacteria that is capable of biodegrading oil with the Proteinaceous Dispersants, either in pellet or powder form.

Further details, objects, and advantages of the present invention will be apparent through a review of the following Examples.

EXAMPLE I

Preparation of a Preferred Proteinaceous Dispersant

Dried oats were ground using conventional techniques. As will be understood, in the grinding process, a broad spectrum of particle sizes are formed, from "fines" to "roughs," which are separated, one from the others, through conventional sieving apparatus. The fines had a particle size range from about 1 to about 100 μm, and the roughs had a particle size range from about 100 to about 600 μm.

Generally, fines are suitable for refined emulsion preparation, and roughs may be appropriately used as the Proteinaceous Dispersant materials. Accordingly, the roughs were collected and placed in a vat containing hexane and stirred for between 1 to 3 hours. The hexane solubilized the lipids in the particles.

Thereafter, the solution was centrifuged at 4500×gravity to layer out the insoluble proteinaceous materials. Next, the hexane was carefully decanted and the solid materials were air dried at room temperature and at reduced humidity (i.e., relative humidity not exceeding 50 percent). Care was taken to ensure that the entire process remained relatively anhydrous.

EXAMPLE II

Preparation of Synthetic Seawater

Synthetic seawater for use in experiments of the present invention was prepared in the following manner:

| Ingredient | Concentration (g/L) |
| --- | --- |
| NaCl | 17.10 |
| $MgCl_2.6\ H_2O$ | 7.73 |
| $Na_2SO_4$ | 2.85 |
| $CaCl_2.2\ H_2O$ | 1.06 |
| KCl | 0.48 |
| $NaHCO_3$ | 0.14 |

Following dissolution of all ingredients, the solution is adjusted to pH 8.0±0.1 with concentrated hydrochloric acid or sodium hydroxide. As will be appreciated, this formulation is identical to that specified for dispersant performance testing by the U.S. Environmental Protection Agency (the "EPA"). See 40 CFR, Part 300, Subpart J.

EXAMPLE III

Protocol for Testing Oil Dispersion and Emulsification Properties of the Proteinaceous Dispersants A test protocol was designed that combines features of the EPA's standard method and the Labofina (rotating flask) method to evaluate the oil dispersion and emulsification properties of the Proteinaceous Dispersants.

In general, a two-liter beaker containing 1 L of synthetic seawater (prepared in accordance with Example II) is placed in a Model G76 orbital shaker (New Brunswick Scientific, Edison, N.J.). For tests run above or below room temperature, the bath is filled with water to a level which covers the bottom portion of the 2 L beaker, approximately to the level of the water inside the beaker, and the water bath is maintained at the desired temperature either by means of the shaker's internal heater or by an external circulating chiller or heater. The seawater is allowed to reach thermal equilibrium with the water bath before proceeding.

Standard curves for test oils were obtained as follows: Approximately. 0.07 g of oil was added to a 10.0 mL volumetric flask, which was then filled to the mark with chloroform. Dilutions were made with the following concentrations of oil: 3500, 1750, 875, 350, 175, and 87.5 mg/L. Absorbance at 620 nm was measured for all solutions, as well as for a chloroform blank, and a standard curve for the oil was calculated by the method of least squares.

Oil (1.0 g) was added dropwise to the water. The dispersing agent was then sprinkled onto the oil slick. The shaker was started immediately and run at approximately 140 rpm, or about 40% of full scale. This speed was chosen because it appears to yield the most realistic wave action in the beaker without causing spillage. The shaker was stopped after 60 min and a grab sample (ca. 50 mL) was taken from 4–5 cm below the water surface using a large dropper. Exactly 25.0 mL of this sample was pipetted into a separatory funnel containing 25.0 mL of chloroform, and the pipet was rinsed by drawing the chloroform into it and ejecting it back into the funnel. The funnel was then stoppered and shaken for 60 s. The water and chloroform layers were allowed to separate, and the chloroform layer was drawn off and filtered through anhydrous sodium sulfate. A sample of the chloroform layer was taken and its absorbance was read at 620 nm. The concentration of the oil in the chloroform (and therefore in the water sample) was calculated from a standard curve. Percent efficiency is defined as:

$$\%\ \text{Eff.} = \frac{(\text{mg oil/L calculated from absorbance})}{(\text{mg oil originally added to 1 L water})} \times 100\%$$

It has been found that one gram is the optimum amount of test oil to use. If larger amounts of oil are used, so that the water:oil ratio falls below about 1000, the percent efficiency begins to fall off; the dispersal process appears to be water-limited under those conditions. If the quantity of oil is less than 1 g, the amount of oil lost by adhesion to the inner surface of the beaker above the water line becomes significant.

Normally, a single 25.0 mL sample of the oil-water mixture was taken, since replicate analyses indicated that, in general, the oil and water were well-mixed, and the sampling error was small. However, with certain viscous oils, such as No. 6 Fuel Oil, the dispersed drops were larger and there was a greater sampling error. For these oils, two or more replicate samples were extracted and the average oil content reported.

EXAMPLE IV

Comparative Evaluations of Proteinaceous Dispersant Compositions

Comparative tests were conducted on compositions of varying protein content and average particle size to determine the optimum Proteinaceous Dispersant compositions for use in the present invention. These tests covered 6 compositions of Proteinaceous Dispersant: (i) A Grade (15–20% protein, 1–10 $\mu$m average particle size); (ii) B Grade (20–30% protein, 100–600 $\mu$m); (iii) C Grade (45–50% protein, 1–10 $\mu$m); (iv) D Grade (25–30% protein, 100–300 $\mu$m); (v) E Grade, comprising B Grade with particles larger than 300 $\mu$m removed by sieving; and (vi) F Grade, comprising a blend of A Grade and E Grade (in a 1 to 1 ratio). Each test was conducted at 23° C.

Figure 2:
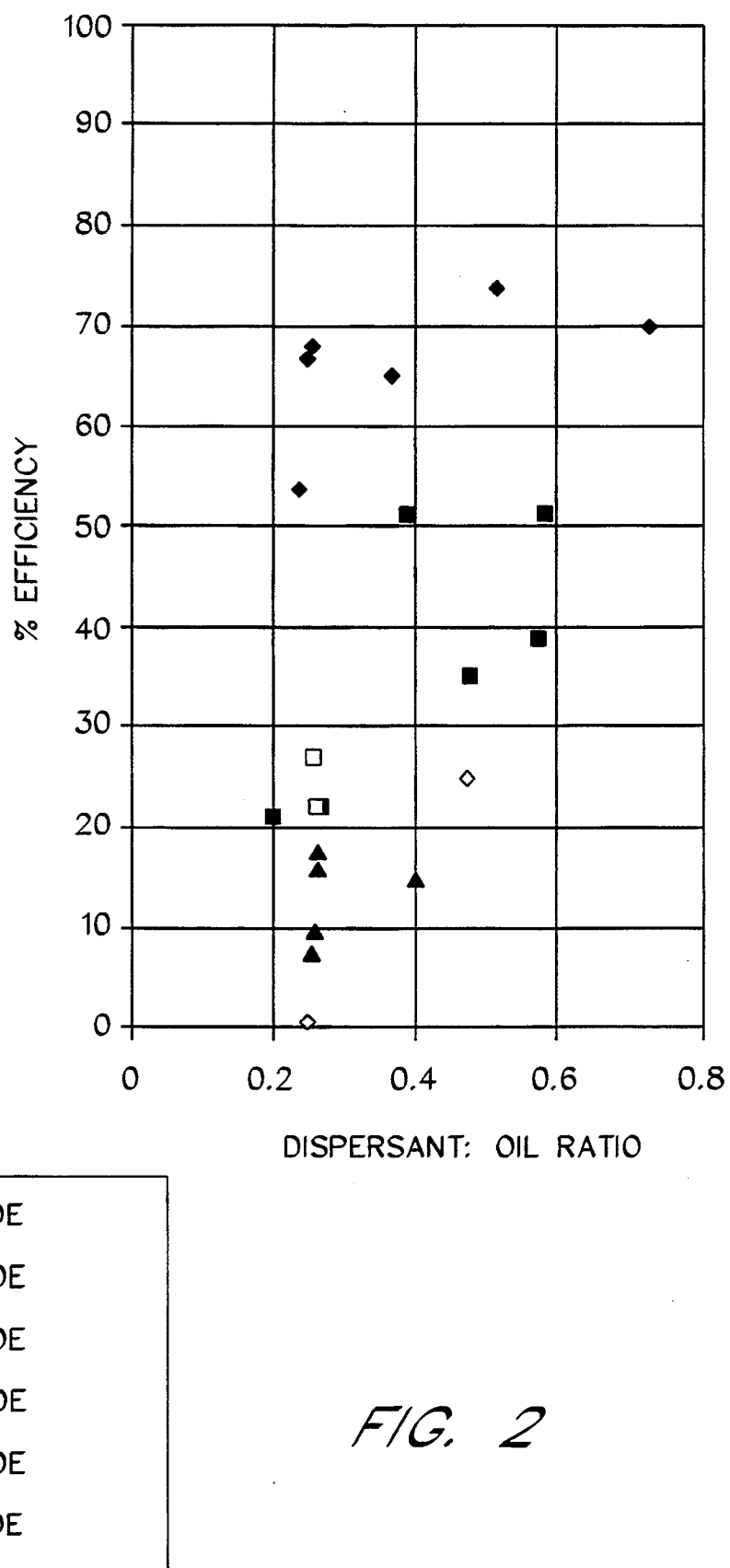

The comparative tests were run on two different oils: Alaskan North Slope crude (obtained from the Shell refinery in Anacortes, Wash.) and the EPA/API standard No. 6 Fuel Oil WP681 (obtained from MSE, Inc., Butte, Mont.). The tests were conducted in accordance with the protocol of Example III at 23° C. The results are shown in FIGS. 1 and 2.

The process of petroleum dispersal by the Proteinaceous Dispersants was found to be essentially identical to their dispersal of other oils. The Proteinaceous Dispersant particles first enter the oil phase. Within seconds the oil begins to break up, as oil is adsorbed at the protein's oleophilic binding sites. At first, medium to large drops of oil scatter into the water, with each drop containing numerous Proteinaceous Dispersant particles. After a few minutes, these drops begin to break up as oil-associated particles scatter into the water phase, each particle taking along several times its weight in oil.

Figure 3:
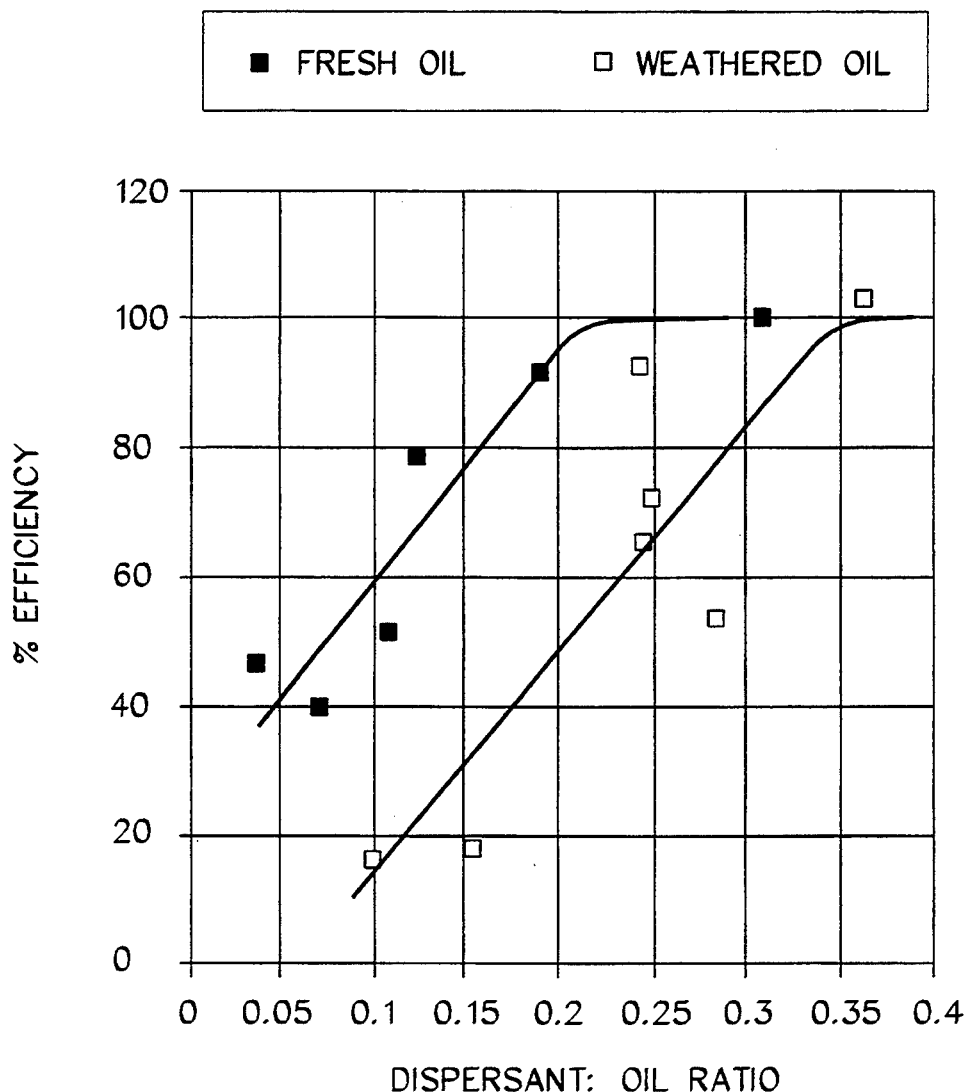

For dispersing the Alaskan crude, the best results were obtained with the E Grade having average particle size 100–300 $\mu$m. The oil dispersal efficiency of E Grade is shown in FIG. 3. One part of the E Grade Proteinaceous Dispersant completely disperses five parts of fresh North Slope crude oil. In the absence of wave action, it penetrates very readily into a floating 1 cm layer of oil and spreads readily through the oil phase without sedimenting into the water below. With gentle wave action, the oil quickly breaks up into small droplets and disperses into the water phase.

Figure 4:
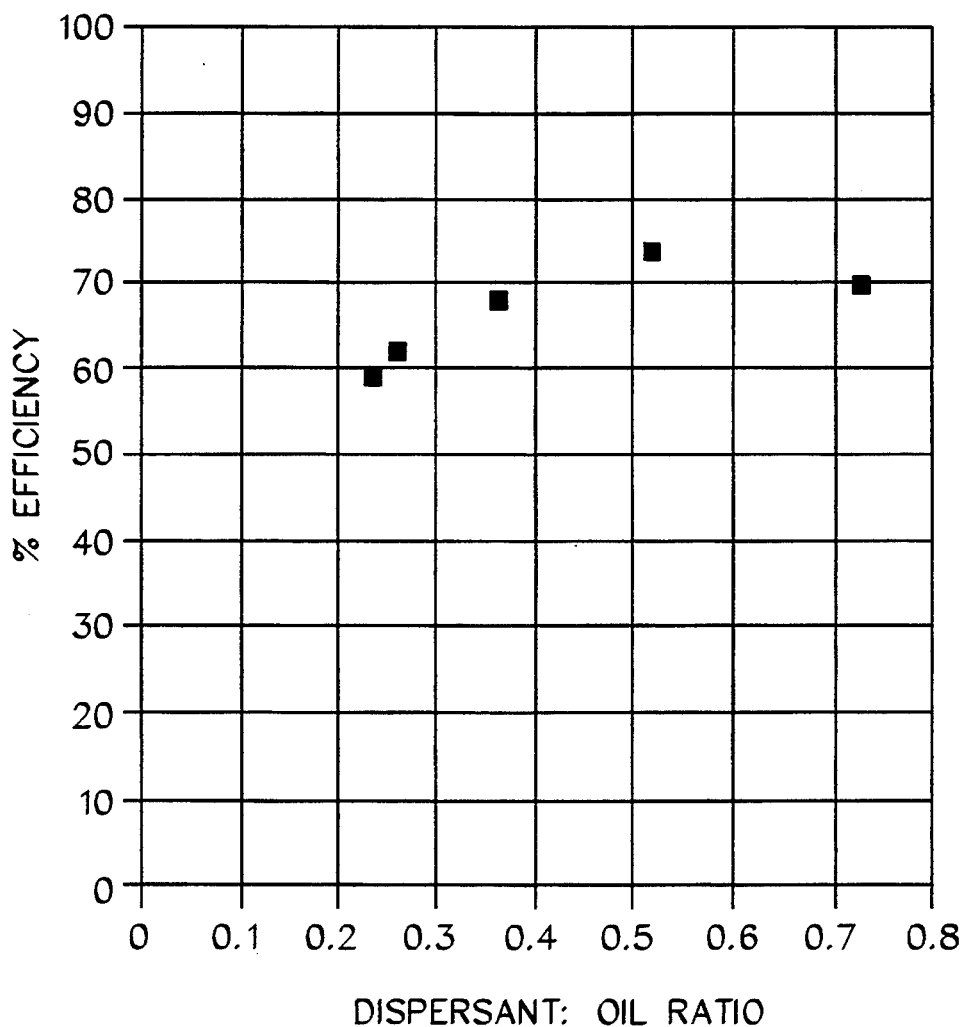

Dispersal tests were also performed on No. 6 Fuel Oil at 23° C. One change was made to the protocol of Example III for No. 6 oil: the Proteinaceous Dispersants were allowed to contact the fuel oil for 3 minutes (as in the standard EPA method) before the start of agitation. The best grade of Proteinaceous Dispersant for dispersing No. 6 oil was the C Grade Proteinaceous Dispersant. It demonstrated a maximum attainable percent efficiency for residual oil of about 70; this degree of dispersal was obtained at a Proteinaceous Dispersant to oil ratio of about 0.25 and, after this point, higher dispersal could not be obtained no matter how much Proteinaceous Dispersant was added. The results of tests using the C Grade Proteinaceous Dispersant on the No. 6 Fuel oil are shown in FIG. 4.

It will be understood that the dispersal properties of No. 6 oil are quite different from those of fresh or weathered crude oils. To disperse oil, the Proteinaceous Dispersants must penetrate the oil's surface and be wetted by the oil, thus enabling the oil/Proteinaceous Dispersant mixture to form an emulsifiable concentrate. The very high viscosity of No. 6 oil retards the mixing or absorption process; the oil molecules presumably are slow to wet the Proteinaceous Dispersant particles and bind to the hydrophobic sites. As the Proteinaceous Dispersants adsorb the oil, the mixture becomes even more viscous. Thus, it appears that at some point the Proteinaceous Dispersant particles no longer penetrate the oil surface.

A set of preliminary oil dispersal tests was also conducted using fresh water. The performance of Proteinaceous Dispersant in fresh water was found to be substantially the same as in sea water.

EXAMPLE V

Comparative Evaluation of a Soy Protein Proteinaceous Dispersant Composition Test samples of a soy protein Proteinaceous Dispersant were prepared in accordance with Example I, through extracting two samples of ground soy beans (−50−−200 mesh, and −200 mesh, respectively) with hexanes. The quantities prepared were sufficiently small that the extracted soy protein was vacuum filtered instead of centrifuged. The resulting materials were tested for oil dispersal efficiency as described in Example III, where one gram of oil was placed in one liter of synthetic seawater (Example II) and the soy protein Proteinaceous Dispersant was added to the slick. After 60 minutes of agitation, a grab sample was collected and extracted with chloroform. Absorbance of the chloroform extract was read at 620 nm. The results, expressed in percent efficiency, are shown in the following Table I.

TABLE I

| | OIL DISPERSING EFFICIENCY FOR SOY PROTEINACEOUS DISPERSANT | |
|---|---|---|
| Particle Size | Percent Efficiency for 0.1 g of the Soy Proteinaceous Dispersant | Percent Efficiency for 0.2 g of the Soy Proteinaceous Dispersant |
| −50/+200 mesh | 25.5 | 5.9 |
| −200 mesh | N/A | 13.8 |

While the soy protein did not perform as well as oat protein as the Proteinaceous Dispersant, it is effective. Interestingly, the soy material appears to undergo more agglomeration than oats, as seen by the decline in percent efficiency for the −50/+200 mesh soy material when the quantity was increased.

EXAMPLE VI

Effects of Different Cruded Oils

Besides the Alaskan crude, two other crude oils were used in tests with the Proteinaceous Dispersants: Rangely crude from Colorado and Brent Blend crude from the North Sea. North Slope crude and the Rangely and Brent crudes were first weathered by being exposed to the open air at room temperature for one to two weeks until they had lost about 20% of their weight. When spilled on water, oil rapidly loses its light fractions by evaporation. By the time dispersants are applied, most spilled oil has undergone this weathering process to some extent. Most weathering occurs in the first 24 to 48 hours after the oil is spilled, and weathering is essentially complete in 1 to 2 weeks. Weathered oil was therefore included in these tests.

Figure 5:
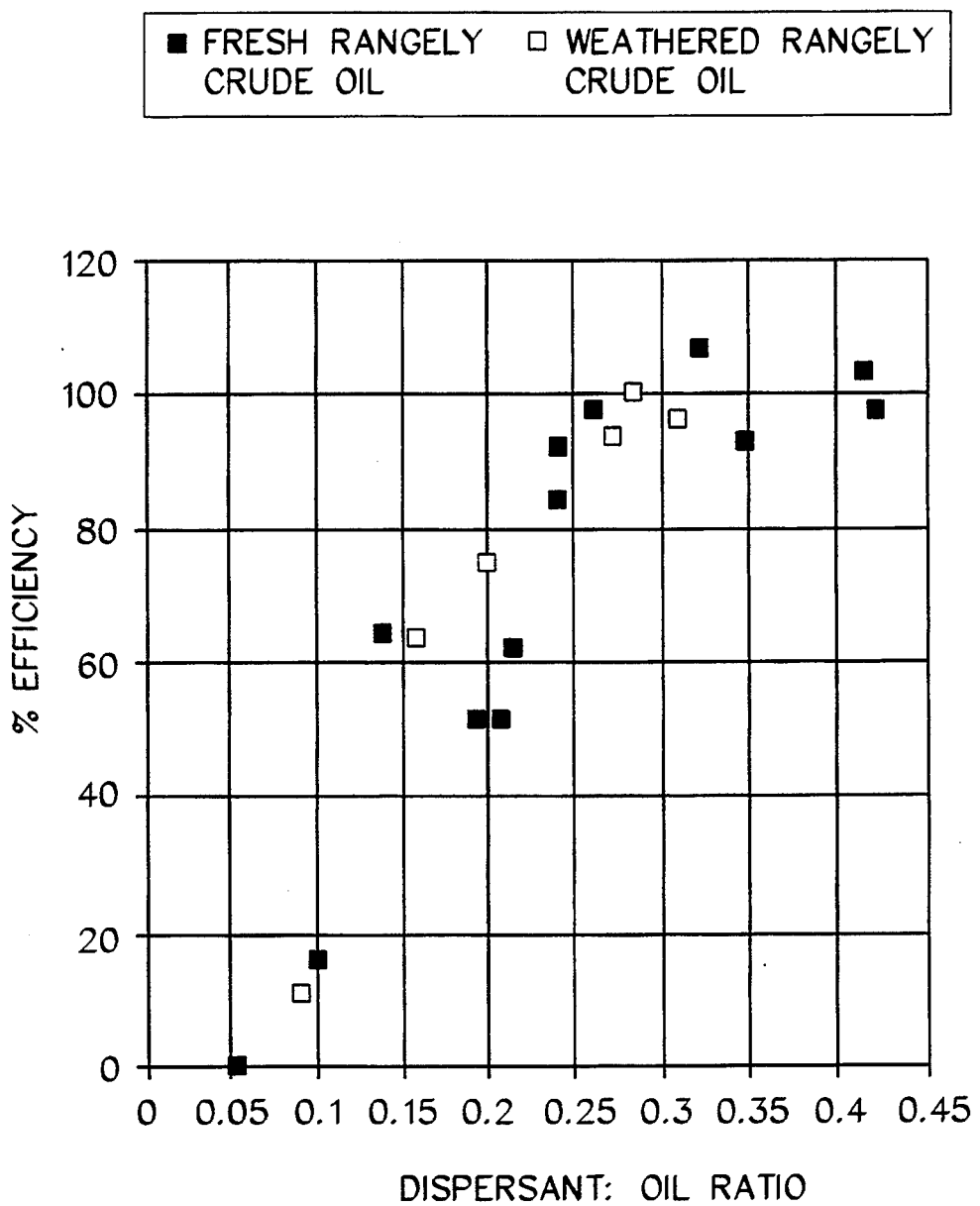
Figure 6:
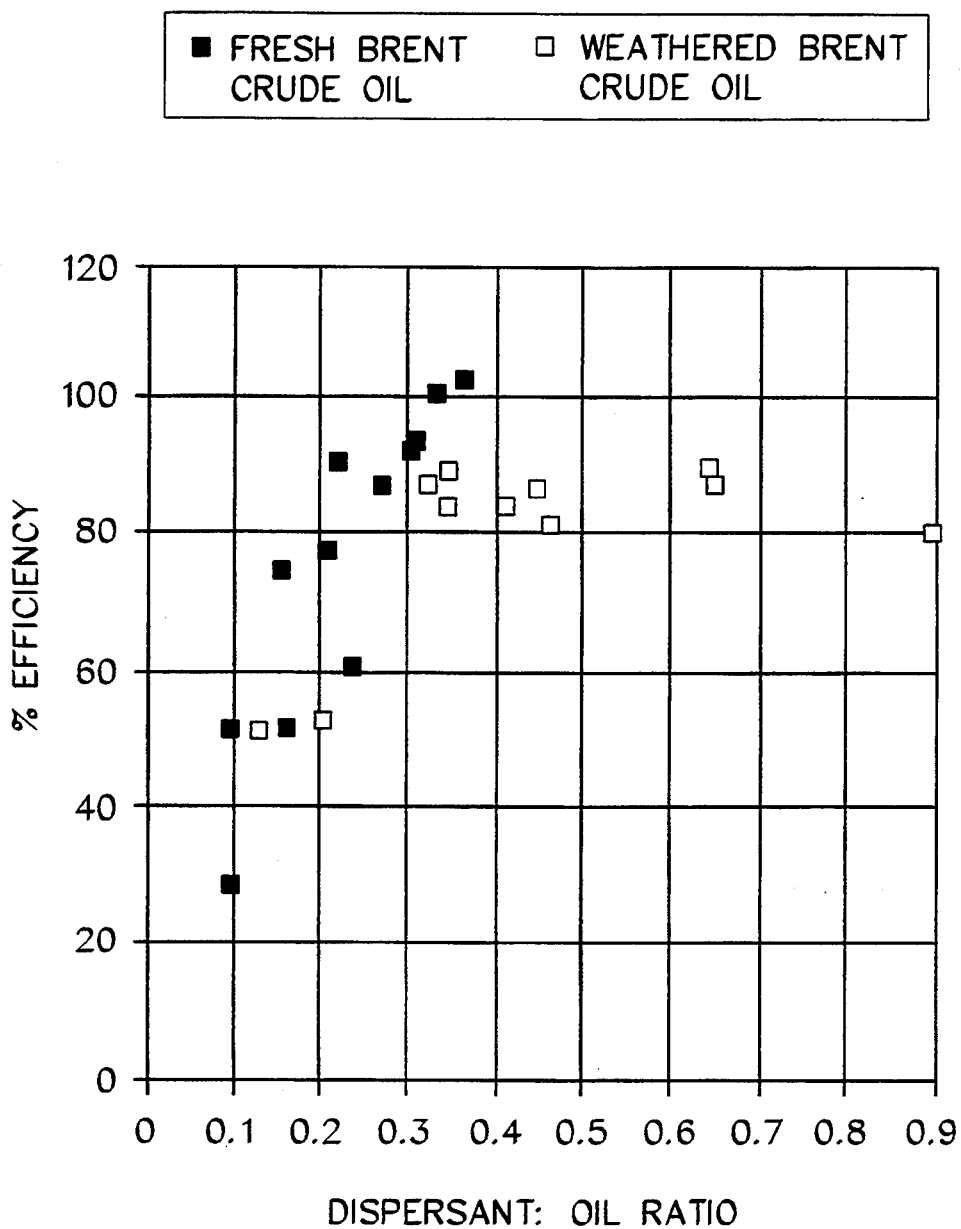

The test results for the Proteinaceous Dispersants with the different oils in both fresh and weathered states are summarized in Table II, and the detailed plots of percent dispersal efficiency are shown in FIGS. 1, 5, and 6.

TABLE II

DISPERSAL OF FRESH AND WEATHERED CRUDE OILS BY NURTURE OIL DISPERSANT

| Oil Tested | Dispersant:Oil Ratio Yielding 100% Efficiency |
|---|---|
| Fresh North Slope | 0.22 |
| Weathered North Slope | 0.33 |
| Fresh Rangely | 0.28 |
| Weathered Rangely | 0.28 |
| Fresh Brent Blend | 0.32 |
| Weathered Brent Blend | 0.32** |

**The maximum dispersal efficiency obtained for weathered Brent Blend Crude was 90%.

EXAMPLE VII

Mousse Dispersal

The ability of the Proteinaceous Dispersants of the present invention to disperse oil mousses was also examined. An oil mousse is formed when oil on water is agitated by wave and wind action and an emulsion-like system forms that is exceptionally sticky. Typically, such mousses are a nemesis of oil dispersants; they are poorly dispersed by conventional dispersants, if at all.

Alaska North Slope crude oil was converted to mousse, a water-in-oil emulsion, as follows: The crude was left open to the air for one day to allow it to weather somewhat. It was then mixed with an excess of synthetic seawater at high speed in a blender. After 10 min total mixing time a stable chocolate-brown mixture had formed. This mousse, which contained about 60% water by weight, was extremely sticky and adhered readily to all surfaces with which it came in contact. After a week's storage at approximately 25° C., it showed no signs of syneresis.

Figure 7:
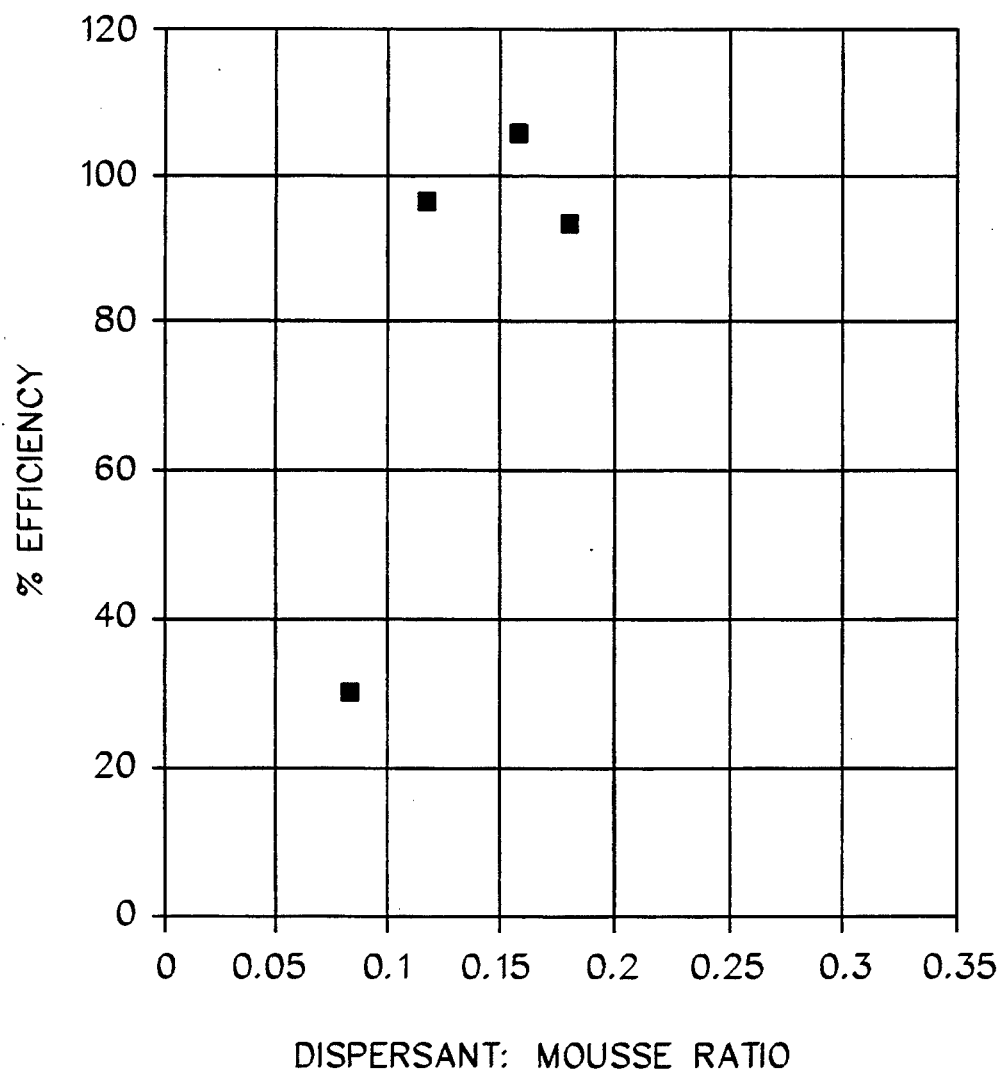

E Grade Proteinaceous Dispersant was tested as a dispersant for the mousse. The results are shown in FIG. 7. One part of the E Grade Proteinaceous Dispersant completely dispersed about 7 parts mousse. This corresponds to a Proteinaceous Dispersant:oil ratio of approximately 0.35, which is close to the ratio that was previously found to result in complete dispersal of well-weathered North Slope crude. Thus, mousse formation is found to have little or no effect on the Proteinaceous Dispersant's ability to disperse oil.

EXAMPLE VIII

Temperatures Studies

Figure 8:
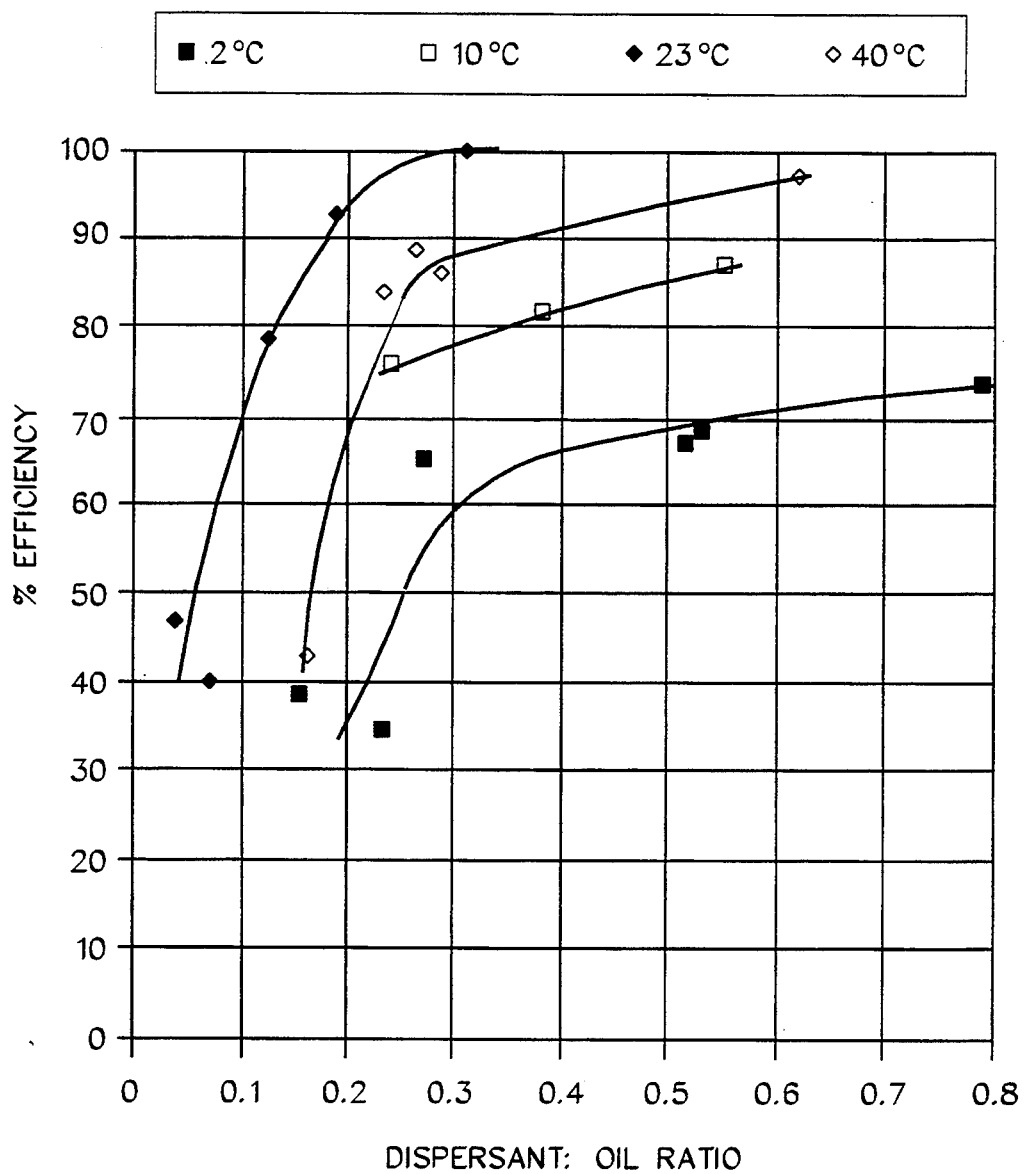
Figure 9:
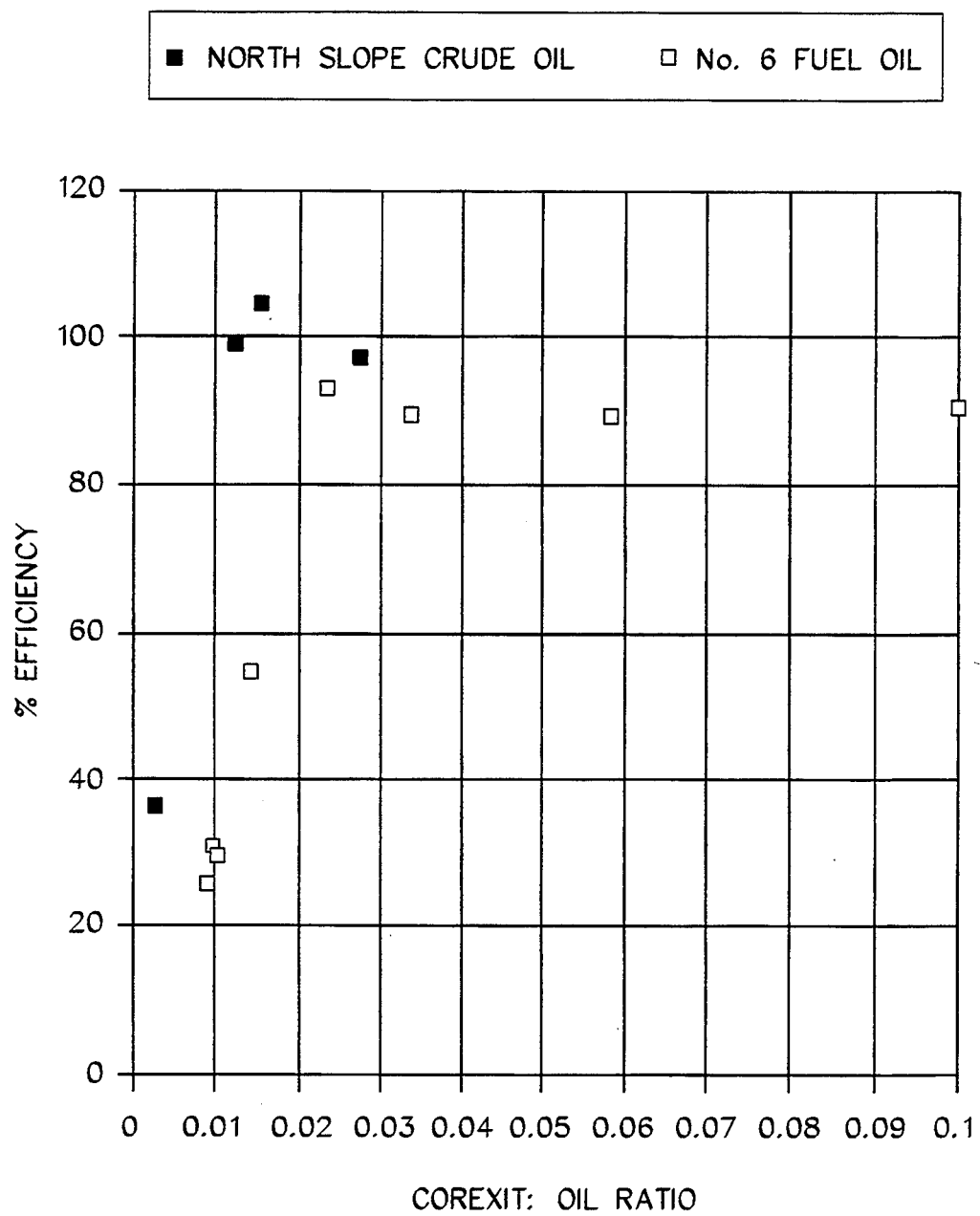
Figure 10:
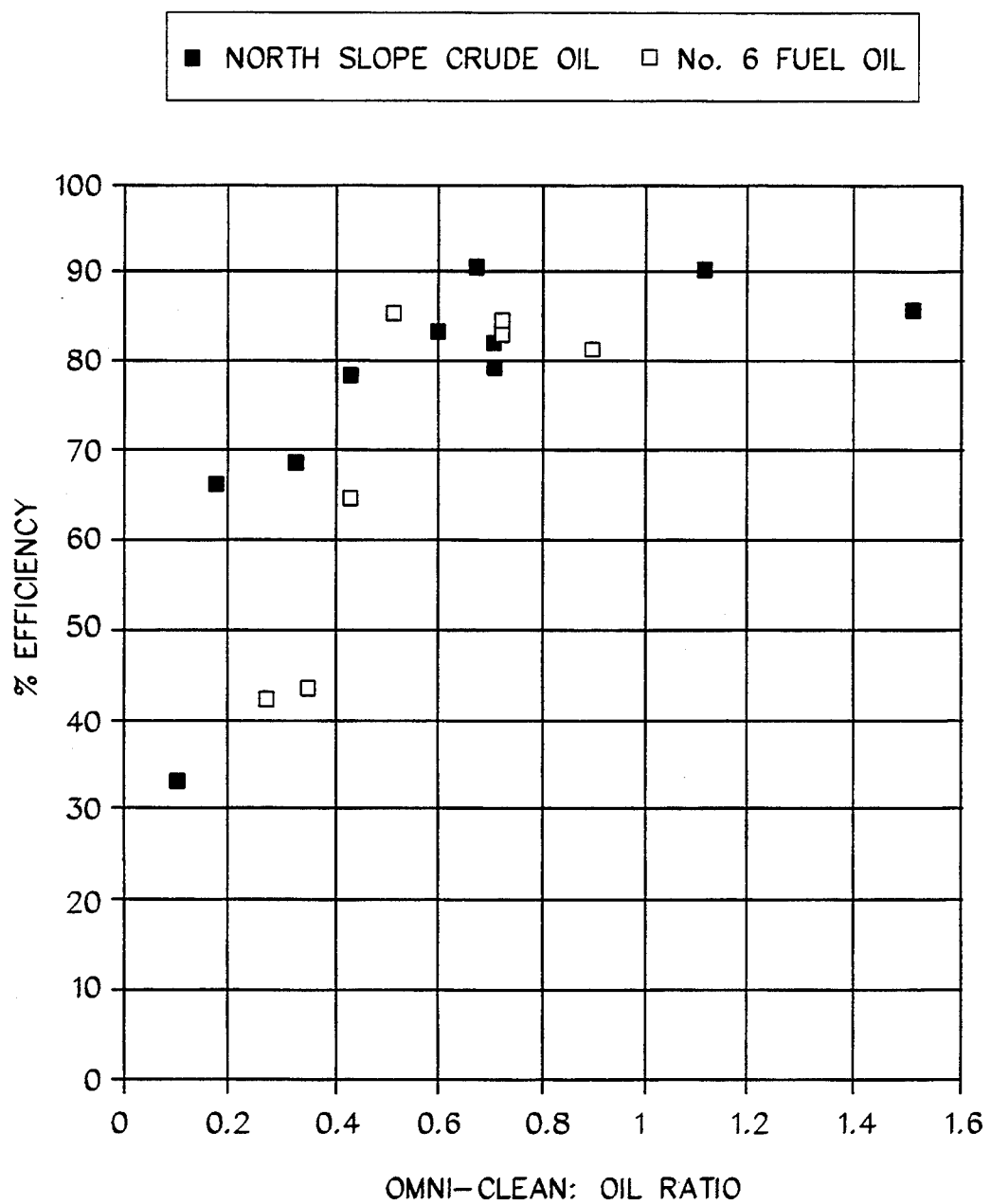
Figure 11:
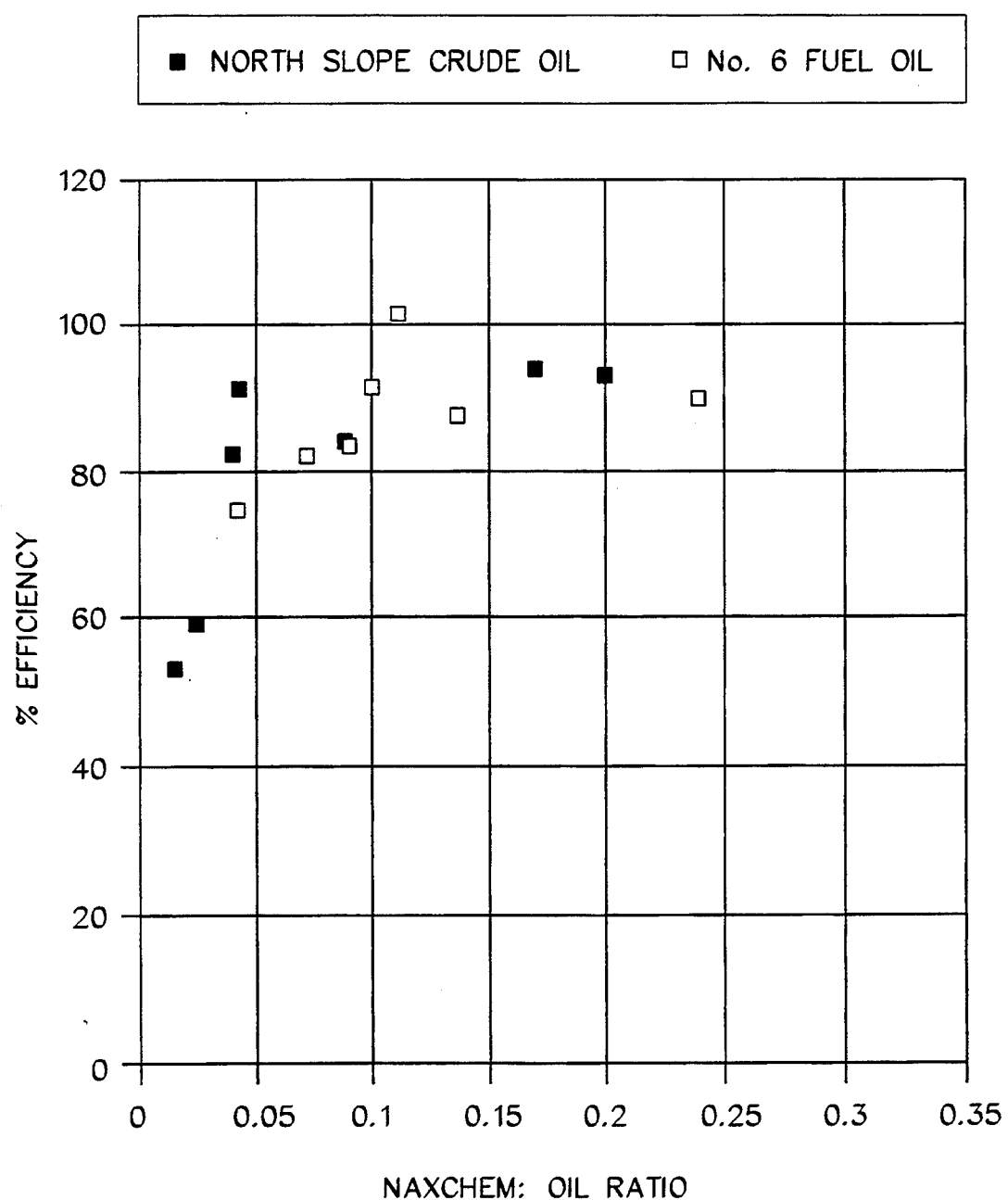
Figure 12:
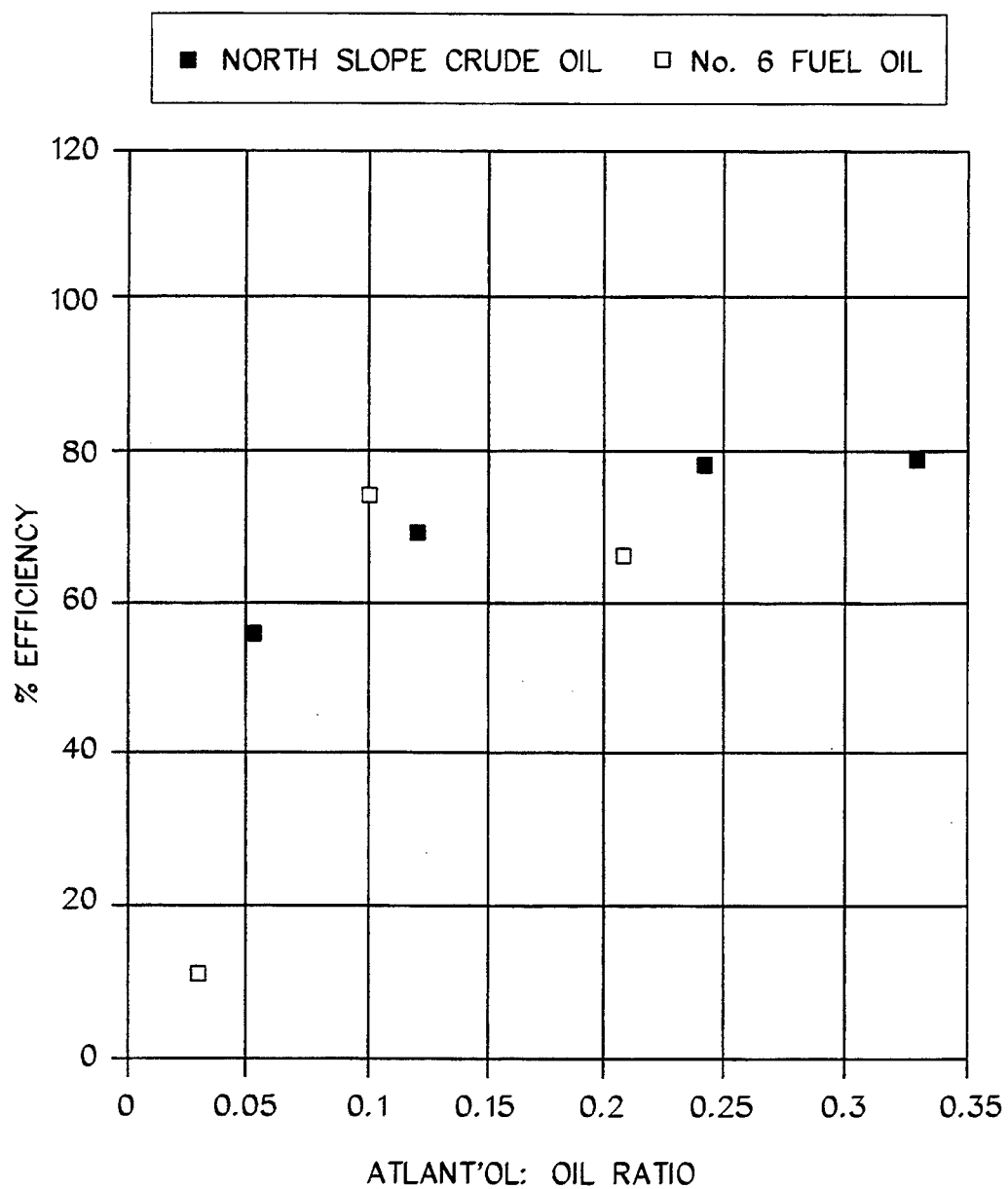
Figure 13:
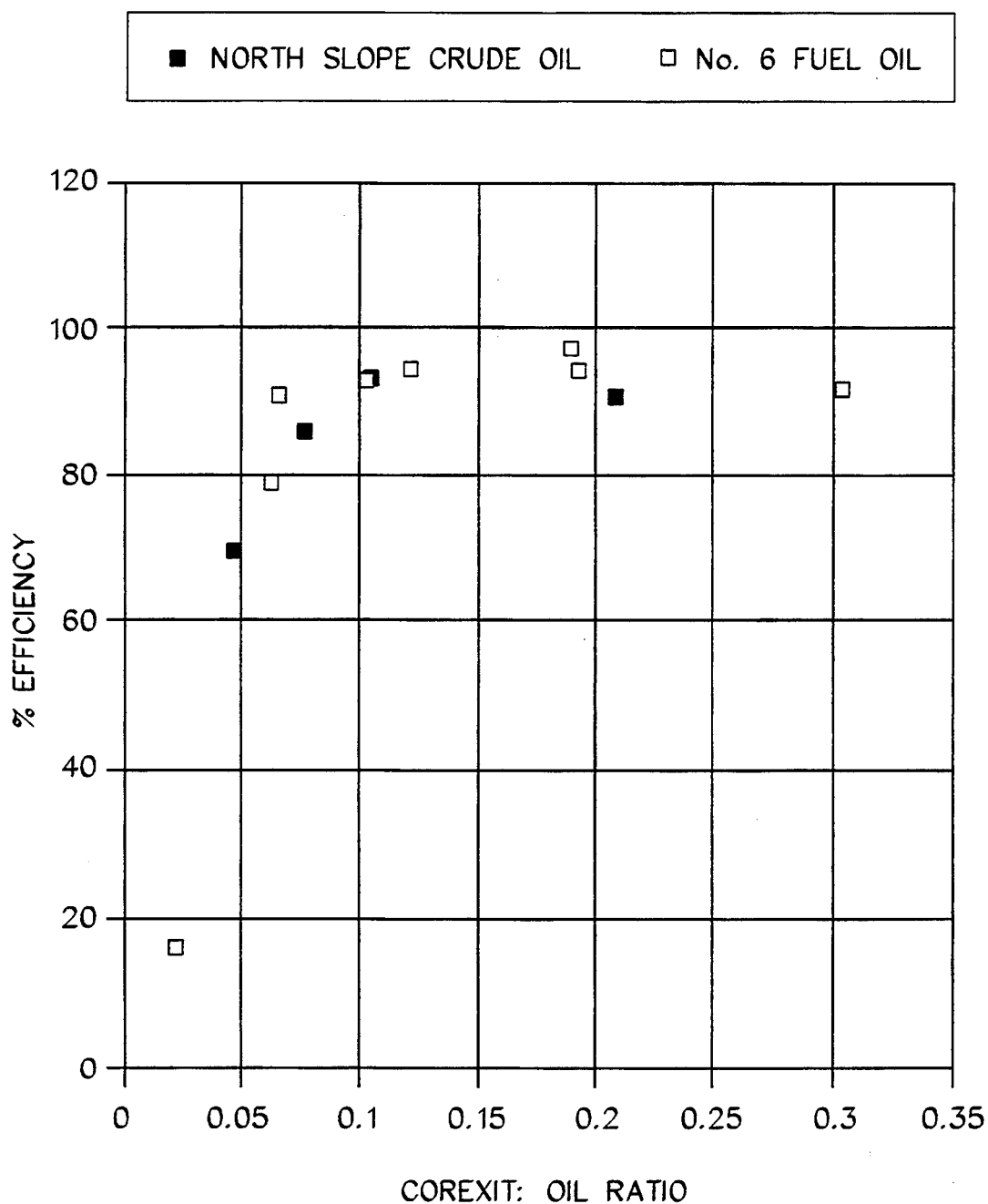
Figure 14:
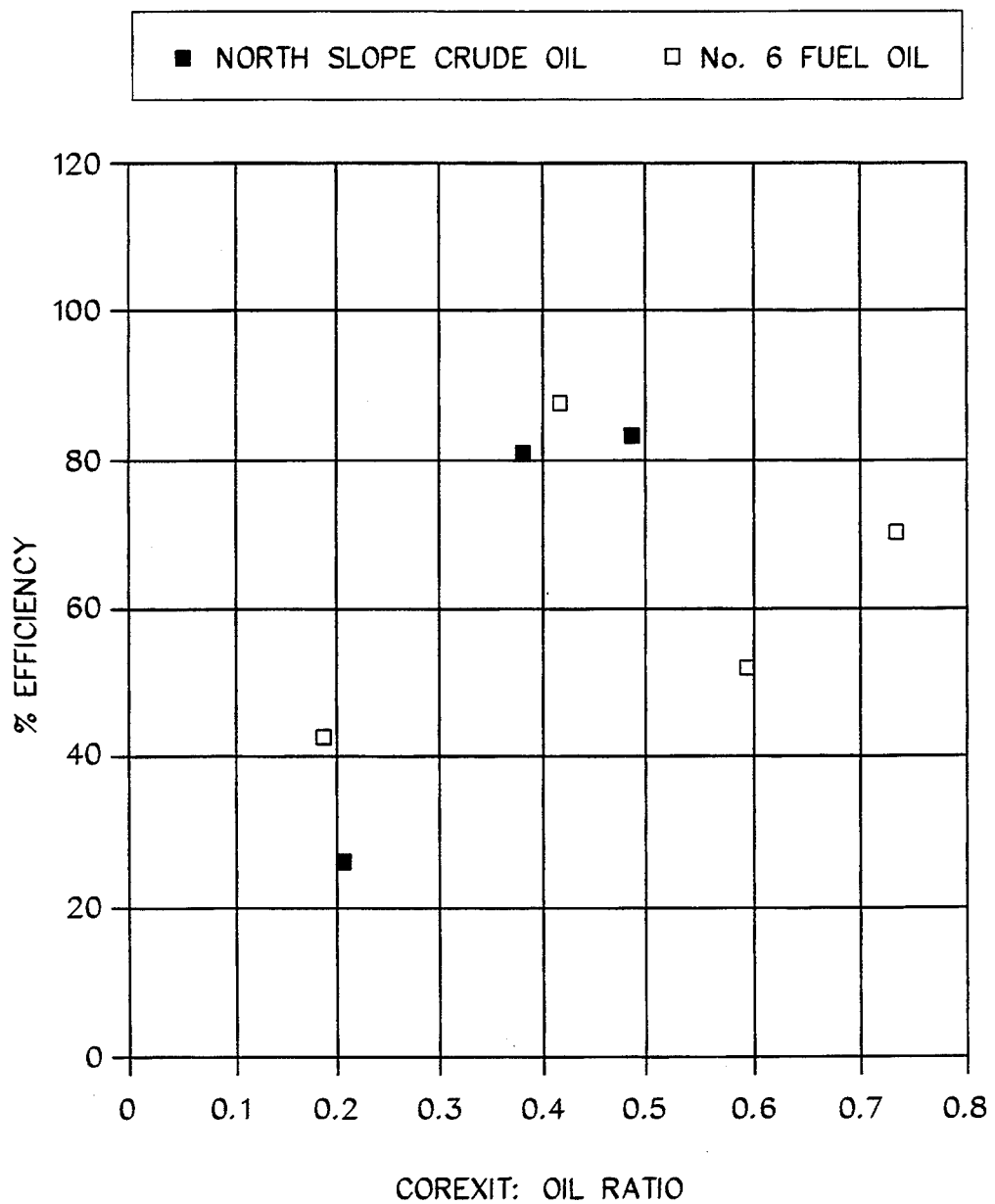

The effects of temperature on the oil dispersing ability of the Proteinaceous Dispersants of the present invention was also examined. Accordingly, the protocol of Example III was followed with E Grade Proteinaceous Dispersant and North Slope crude at 2°, 10°, and 40° C., in addition to the previous runs at 23° C. Results of runs at all four temperatures are shown in FIG. 8. The portion of the oil which can be dispersed by the Proteinaceous Dispersant is seen to be a function of temperature, as summarized in Table III.

TABLE III

DISPERSAL OF NORTH SLOPE CRUDE AS A FUNCTION OF TEMPERATURE

| Temperature (°C.) | Maximum Dispersal (%) |
|---|---|
| 2 | 65 |
| 10 | 76 |

TABLE III-continued

DISPERSAL OF NORTH SLOPE CRUDE AS A FUNCTION OF TEMPERATURE

| Temperature (°C.) | Maximum Dispersal (%) |
|---|---|
| 23 | 100 |
| 40 | 87 |

Between 2° and 23°, as the oil became less viscous, it also became easier to disperse. The lower apparent efficiency at 40° was probably due to evaporation of some of the oil at that temperature.

EXAMPLE IX

Comparative Tests of Commercial Oil Dispersants

Six commercially available oil dispersants were tested for dispersal of North Slope crude and No. 6 Fuel Oil, using the protocol of Example III. Each of the dispersants are primarily surfactant products. The products tested include Corexit® 9527 (Exxon), a leading surfactant-solvent product for oil dispersal; Naxchem® Dispersant K (formerly known as Conco Dispersant K and now sold by Ruetgers-Nease), a product consisting primarily of surfactants and alcohols; Atlant'ol® AT-7 (Aspra, Inc.), a water-based product; Omni-Clean® OSD (Delta Omega Technologies), a water-based product containing synthetic surfactants and fatty acid soaps and marketed as a safe, low-toxicity product; Corexit 9550 (Exxon), a solvent based product; and Corexit 7664 (Exxon), a product formerly marketed as an open-sea dispersant but now sold mostly as a beach cleaner. Corexit 7664 was included in this study as representative of old oil-spill technology. Finasol® OSR-7, a dispersant which has been included in several published studies, was to have been included in these tests, but the product has been withdrawn from the market and is no longer available.

Table IV compares the dispersal efficiencies of the above products on North Slope Crude with those of the C Grade and E Grade Proteinaceous Dispersants. Table V compares the same products' performance on No. 6 Fuel Oil. The dispersal efficiencies of the commercial products at different usage levels are plotted in FIGS. 9 through 14.

TABLE IV

DISPERSAL EFFICIENCIES FOR ALASKA NORTH SLOPE CRUDE

| Oil Dispersant | Minimum Dispersant:Oil Ratio for Maximum Dispersal Efficiency | Maximum Dispersal Efficiency (%) |
|---|---|---|
| E Grade | 0.22 | 100 |
| C Grade | 0.5 | 100 |
| Corexit 9527 | 0.01 | 100 |
| Omni-Clean OSD | 0.5 | 85 |
| Naxchem Dispersant K | 0.04 | 90 |
| Atlant'ol AT-7 | 0.2 | 80 |
| Corexit 9550 | 0.07 | 90 |
| Corexit 7664 | 0.35 | 80 |

TABLE V

DISPERSAL EFFICIENCIES FOR NO. 6 FUEL OIL

| Oil Dispersant | Minimum Dispersant:Oil Ratio for Maximum Dispersal Efficiency | Maximum Dispersal Efficiency (%) |
|---|---|---|
| E Grade | 0.4 | 40 |
| C Grade | 0.4 | 70 |
| Corexit 9527 | 0.02 | 90 |

TABLE V-continued

DISPERSAL EFFICIENCIES FOR NO. 6 FUEL OIL

| Oil Dispersant | Minimum Dispersant:Oil Ratio for Maximum Dispersal Efficiency | Maximum Dispersal Efficiency (%) |
|---|---|---|
| Omni-Clean OSD | 0.5 | 85 |
| Naxchem Dispersant K | 0.10 | 90 |
| Atlant'ol AT-7 | 0.10 | 70 |
| Corexit 9550 | 0.07 | 90 |
| Corexit 7664 | 0.4 | 70 |

As will be seen, a given quantity of E Grade Proteinaceous Dispersant dispersed more crude oil than an equal amount of Omni-Clean OSD, Atlant'ol AT-7, or Corexit 7664, and less than a like amount of Corexit 9527, Naxchem Dispersant K, or Corexit 9550.

EXAMPLE X

Effect of the Proteinaceous Dispersants on Biodegradation of Oil

To study the effect, if any, of the Proteinaceous Dispersant on biodegradation, a three-week study was performed using known petroleum-degrading bacteria. The bacteria were obtained from Prof. Phillip Fedorak of the Microbiology Department at the University of Alberta (Edmonton, Alberta). These bacteria came from cultures originally isolated in 1979 from Puget Sound and the Strait of Juan de Fuca. These bacteria were found to degrade both saturated and aromatic components of Prudhoe Bay crude oil. Since 1979, the bacteria have been cultured in a medium containing Prudhoe Bay crude. An inoculum of these oil-degrading bacteria was sent to us by Dr. Fedorak in December 1991, and a degradation study was performed on North Slope Alaskan crude (which is probably quite similar to the Prudhoe Bay crude utilized by Dr. Fedorak).

Because of the use of crude oil in sea water as a substrate, it is not feasible to culture the bacteria on agar or any other standard microbiological medium. Moreover, the effectiveness of the bacterium at degrading oil cannot be judged by standard methods, such as colony counts. Instead, oil was extracted from each culture according to Fedorak's method and analyzed by gas chromatography. See Fedorak, et al., Can. J. Microbiol. 27:432 (1981).

The following cultures were prepared to test the ability of the Proteinaceous Dispersants to enhance bacterial degradation of oil:

(1) (Control) 200 mL sterile seawater and 200 μL North Slope crude oil;
(2) 200 mL sterile seawater, 200 μL North Slope crude oil, and 2.00 mL inoculum;
(3) 200 mL sterile seawater, 200 μL North Slope crude oil, 2.00 mL inoculum, and 4.00 mL nitrogen+-phosphorus (N+P) solution;
(4) 200 mL sterile seawater, 200 μL North Slope crude oil, 2.00 mL inoculum, and 48 mg of sterile Proteinaceous Dispersant;
(5) 200 mL sterile seawater, 200 μL North Slope crude oil, 2.00 mL inoculum, and 48 mg of unsterilized Proteinaceous Dispersant.

Each treatment was cultured in a 500 mL Erlenmeyer flask. The nitrogen+phosphorous (N+P) solution was a solution of 0.60M ammonium nitrate and 0.30M sodium phosphate, adjusted to pH 7.95 with sodium hydroxide and sterilized with a sterile 0.2 μm filter. The cultures were agitated at 190 rpm in a water bath maintained at 28° C. in a New Brunswick Model G76 orbital shaker (New Brunswick Scientific, Edison, N.J.). After 21 days, bacterial action was stopped by the addition of 2 mL of 37% hydrochloric acid. Oil was then extracted from the cultures as follows:

Each sample was spiked with 50 μL of a solution of 2 g/L chrysene and 12 g/L squalene in methylene chloride. (These compounds served subsequently as internal standards for gas chromatography.) The sample was then transferred to a 500 mL separatory funnel and extracted with successive 15 mL, 10 mL, and 10 mL volumes of methylene chloride. The extracts were filtered through anhydrous sodium sulfate, the Erlenmeyer flask and sodium sulfate were rinsed with additional methylene chloride, and the volume was made up to 40 mL with methylene chloride. A 10 mL aliquot of the extract was reduced to approximately 1 mL by refluxing at 80°–85° C. using a Kontes Model K-720 000 Tube Heater (Kontes Co., Vineland, N.J.). In order to protect the gas chromatography column, sulfur compounds were removed from the samples with activated copper. Copper (electrolytically purified dust) was activated immediately before use by soaking for 2 min in 37% hydrochloric acid, then rinsed with reagent grade methanol to remove the acid, then with pesticide grade methylene chloride. The concentrated samples (approximately 1 mL) were run into the activated copper in a liquid chromatography column, held for 2 min, then eluted and reduced to 1.0 mL volume with the tube heater.

These samples were then subjected to gas chromatography using a glass capillary column (0.53 mm I.D., 25 m long, OV-1 coating) in a Perkin-Elmer Model 8500 gas chromatograph equipped with a flame ionization detector. The carrier gas was helium flowing at 12 mL/min. The injector inlet temperature was 300° C., and the detector temperature was 350° C. The initial column temperature was 80° C. Upon sample injection, the column was held at 80° C. for 4 min; then the temperature was increased 4 K/min to a final temperature of 270° C. and held at that temperature for 32 min.

Figure 15:
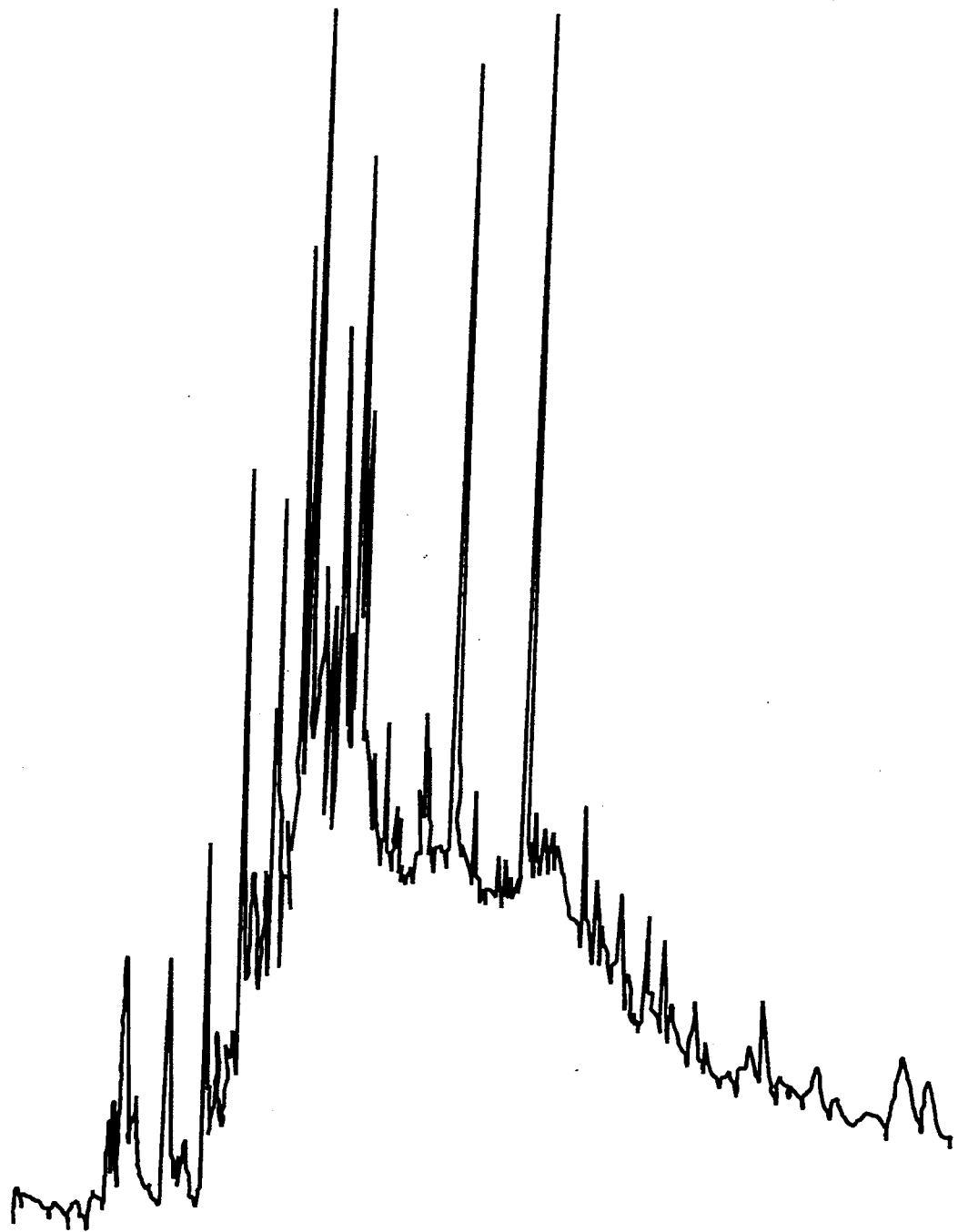
Figure 16:
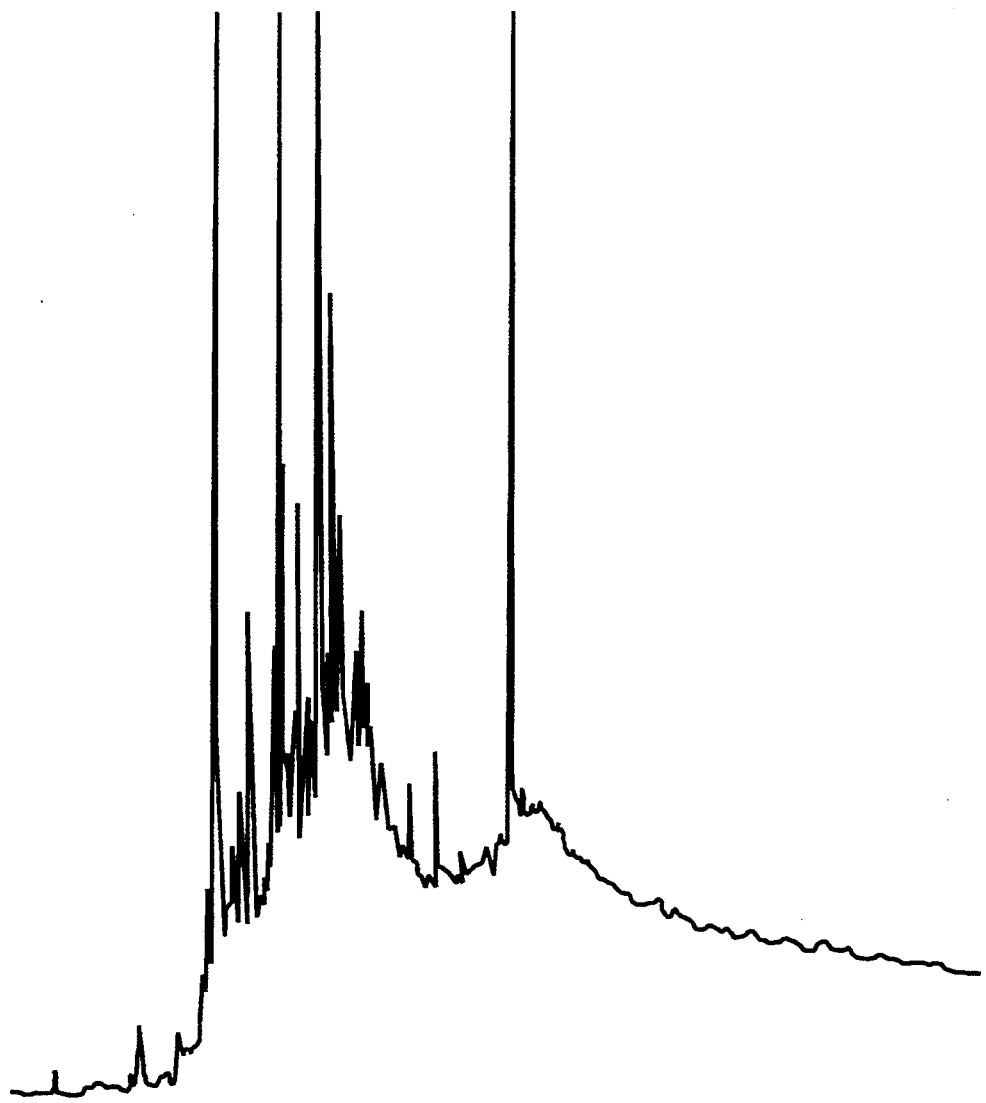
Figure 17:
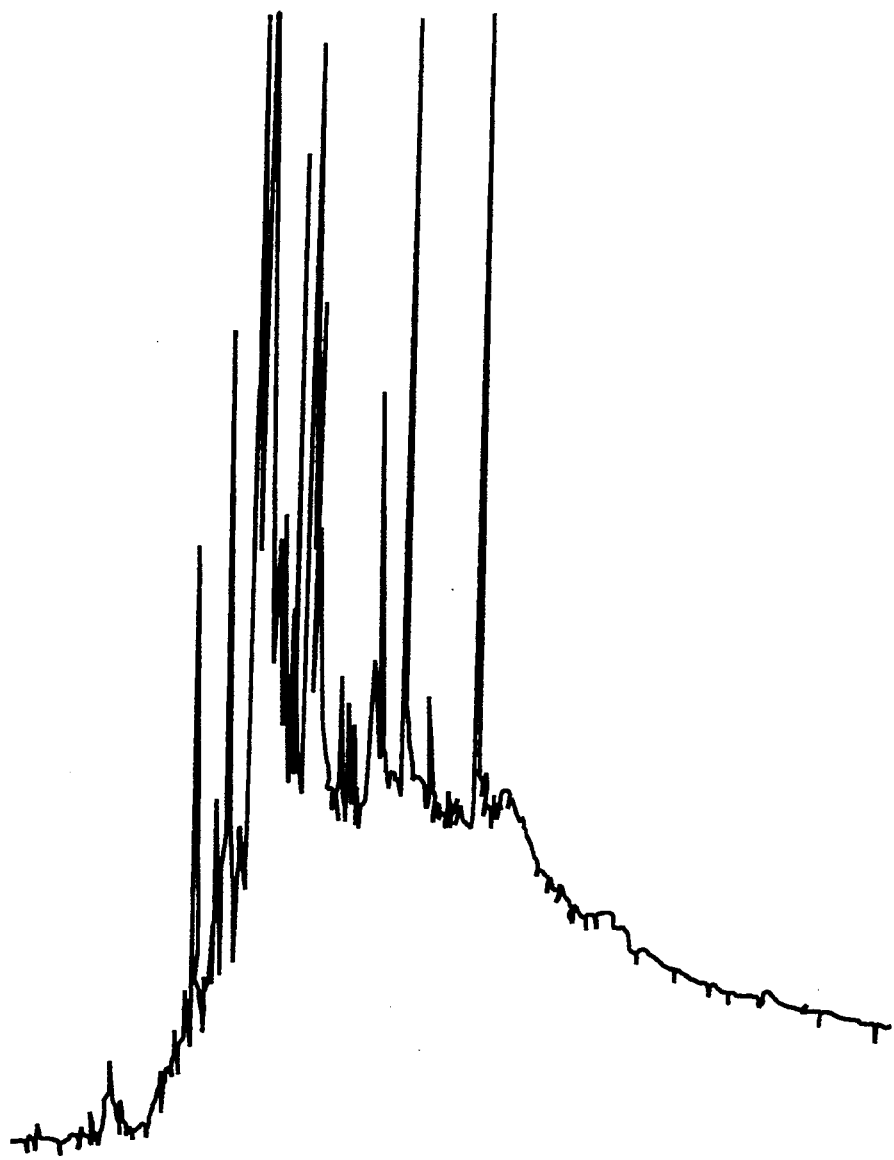
Figure 18:
Figure 19:
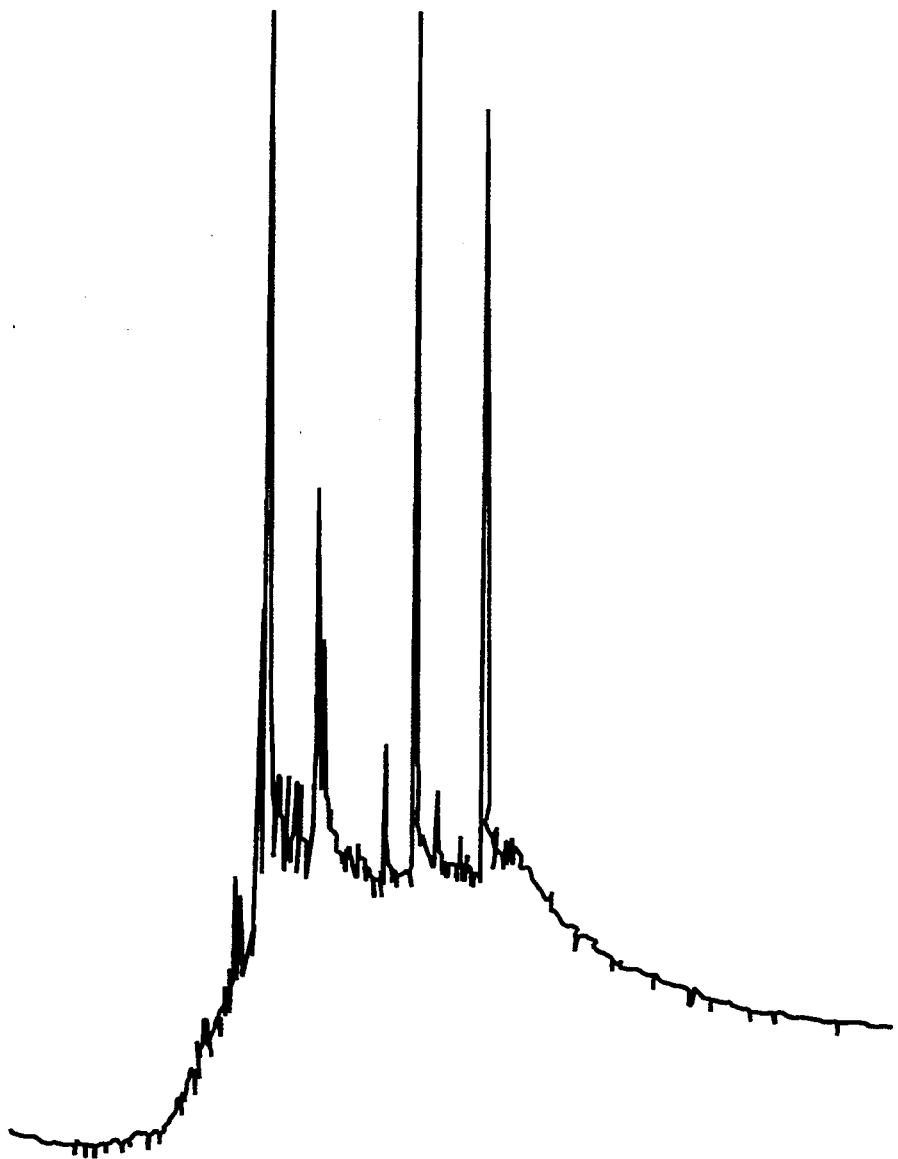
Figure 20:
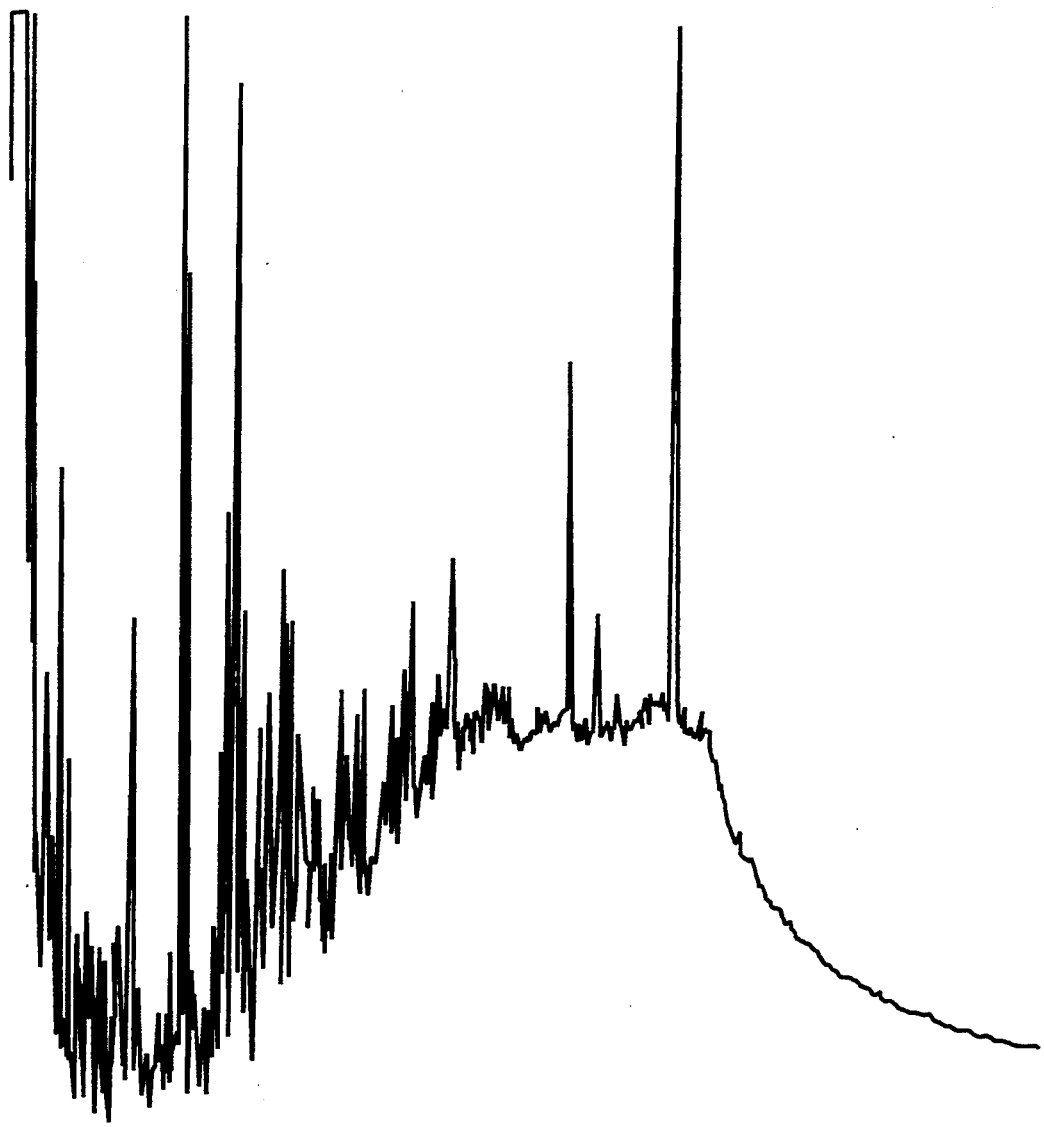

FIGS. 15 through 19 are the chromatograms obtained from treatments 1 through 5, respectively. For comparison, FIG. 20 is a chromatogram obtained from the fresh, unweathered North Slope crude oil. In FIG. 15, the many peaks may be seen corresponding to substances that are still present in crude oil after 21 days of weathering at 28° C. in the absence of oil-degrading bacteria. FIG. 16 shows the effect of oil-degrading bacteria without added fertilizer. In FIG. 17, with added nitrogen and phosphorus nutrients, the bacteria have removed more compounds. FIGS. 18 and 19 show the effects of the Proteinaceous Dispersant. Whether or not the dispersant is sterilized, most of the peaks present in FIG. 15 are missing or greatly reduced. In fact, the degree of reduction achieved with the Proteinaceous Dispersant is larger than that achieved with the N+P fertilizer solution.

Table IX lists several of the principal peaks present in the chromatogram of the control extract (FIG. 15) and compares them with the corresponding peaks in the chromatograms of the other extracts. The areas of the squalene (internal standard) peaks in FIGS. 16 through 19 were normalized to the area of the squalene peak in FIG. 15, and the areas of the other peaks in FIGS. 16 through 19 were adjusted proportionally. In all cases, the areas of the internal standard peaks were within 5% of the average.

These peaks provide examples of different substances present in crude oil and their responses to bacteria. The peaks eluting at 33.33, 37.73 and 53.66 minutes represent compounds that are relatively easy to degrade; even in the absence of added nutrients the peak areas decreased significantly. On the other hand, the compound eluting at 33.56 minutes is one for which bacterial degradation evidently requires nutrients. Degradation of the compound eluting at 52.77 minutes also requires nutrients, and, moreover, the Proteinaceous Dispersants appear to supply a better environment for the bacteria. Finally, the compound eluting at 34.97 minutes appears very hard to degrade with or without nutrients, although the unsterilized Proteinaceous Dispersant in Treatment #5 does appear to be making some progress.

TABLE IX

COMPARISON OF SELECTED PEAK DATA FROM EXTRACTS OF BACTERIAL CULTURES*

| Retention Time (minutes) | #1 Abiotic control (oil, no bacteria) | #2 Oil, bacteria | #3 N + P, oil, bacteria | #4 Sterile Dispersant, bacteria, oil | #5 Unsterile Dispersant, bacteria, oil |
|---|---|---|---|---|---|
| 33.33 | 104 | 55 | 41 | 48 | 40 |
| 33.56 | 123 | 100 | 78 | 58 | 76 |
| 34.97 | 242 | 286 | 215 | 200 | 77 |
| 37.73 | 187 | 82 | 81 | 66 | 91 |
| 52.77 | 124 | 146 | 48 | 0 | 0 |
| 53.66 | 104 | 60 | 0 | 37 | 0 |

*Corrected for internal standard.

There is a simple explanation that probably accounts for the Proteinaceous Dispersant's effect in promoting biodegradation. As noted earlier, E Grade Proteinaceous Dispersant is ca. 20-30% protein, which means it contains about 3-5% available nitrogen; it also contains a significant amount of phosphorus. Thus, the Proteinaceous Dispersant itself is a suitable fertilizer for the bacteria.

Moreover, since the Proteinaceous Dispersant and oil are in close association, all of the nutrients are proximate to the oil, whereas a mineral solution of nutrients would be diffused throughout the water column. In addition, by emulsifying the oil, the Proteinaceous Dispersant increases the area of the oil-water interface, thus making the oil more available for the bacteria. The combination of these three effects makes the Proteinaceous Dispersants more effective than mineral fertilizers in boosting bacterial action.

EXAMPLE XI

Cleaning of Oiled Surfaces

Another application of the Proteinaceous Dispersants of the present invention is in the cleaning of surfaces contaminated by oil from oil spills. For example, frequently wildlife, beaches, and other personal and real property become contaminated with oil as the result of an oil spill. As will be appreciated, with every oil spill, much of the oil winds up on the beaches and on the animals and vegetation that surround the affected area. The Proteinaceous Dispersants of the present invention have shown an ability to cleanse these recipients.

Cleaning of Fowl

To demonstrate this phenomenon, pheasant wings were dipped, twice, into 1600 mL of synthetic seawater in a 2 L beaker through an oil layer containing 10 g of North Slope crude oil. Generally, the Proteinaceous Dispersant was spread on a wing and gently wiped off to agglomerate and remove loose oil, then, a second application was made that was worked into the wing with tap water to emulsify the remaining oil. Finally, the wing was rinsed off with lukewarm water. One wing was treated with Sunlight ® light-duty detergent liquid (a conventional treatment for oiled birds), and rinsed with lukewarm water.

The wings were air-dried, and their weights before and after oiling, as well as their weights after cleaning and drying, were compared. The results are summarized in Table X. Note that all of the wings weighed less after oiling and cleaning than they did at the beginning, indicating that some natural oils were removed, in addition to the crude oil that was removed.

TABLE X

RESULTS OF FIRST SET OF PRELIMINARY BIRD-CLEANING EXPERIMENTS

| Treatment | Initial Wing Weight (g) | Wing & Oil Weight (g) | Final Wing Weight (g) | % of Initial Weight |
|---|---|---|---|---|
| B Grade (3.60 g) | 8.31 | 14.49 | 7.84 | 94.3 |
| B Grade (2.70 g), A Grade (8.00 g) | 8.42 | 14.50 | 7.71 | 91.6 |
| A Grade (12.00 g) | 10.68 | 16.19 | 9.92 | 92.9 |
| Sunlight Liquid Detergent (5.78 g) | 9.09 | 17.02 | 7.74 | 85.1 |
| Dipped in B Grade (not weighed), rinsed, dipped/rinsed again | 12.12 | 21.56 | 11.63 | 96.0 |

All of the wings cleaned with the Proteinaceous Dispersants appeared nearly free of crude oil, although some discoloration was noted. Still, however, all of the wings had a slight odor of oil after drying, except that the "dipped" wing had a strong oil odor. All wings appeared clean, except that the wing treated with the A Grade, alone, appeared greasy and still had visible oil contamination. Sunlight detergent cleaned the wing quite thoroughly, apparently to the extent of removing most or all of the wing's natural oils.

In general, the Proteinaceous Dispersants appeared to remove most of the crude oil, and the B Grade performed better than the A Grade.

Cleaning of Beached Oil

It is believed that beaches may be cleaned in a similar manner to the cleaning of fowl. For example, through spreading the Proteinaceous Dispersants of the present invention on a beach, and scrubbing it into the sand and over the rocks, it is expected that the dispersants will naturally adsorb the oil. Thereafter, the beach front may be rinsed, or in the alternative, the natural wave action will carry the Proteinaceous Dispersant associated oil out to sea, thereby emulsifying it.

What we claimed is:

1. A method for dispersing an oil spill in open water, comprising the steps of:
    providing an dispersant comprising a proteinaceous particulate material comprising milled seed material having oil sorptive and emulsifying properties; and
    applying said dispersant to the oil spill on top of the water to disperse at least a portion of said oil spill wherein said proteinaceous particulate functions as a primary emulsifier for said oil.

2. The method of claim 1, wherein said dispersant is derived from a cereal grain by milling and removal of lipids therefrom.

3. A method for cleaning a solid surface contaminated with petroleum oil, comprising the steps of:
    providing a proteinaceous particulate material comprising milled seed material having oil sorptive and emulsifying properties;
    applying said proteinaceous material to said surface in such a manner that said proteinaceous material becomes intimately associated with said oil and sorbs said oil to form a proteinaceous material/oil combination that is readily dispensable in water; and
    rinsing with water to remove said proteinaceous material and said oil.

4. The method of claim 3, wherein said solid surface is part of an animal.

5. The method o f claim 1, wherein said seeds are selected from the group consisting of legumes and grains.

6. The method of claim 1, wherein said seeds are selected from the group consisting of canola, beans, oats, rape seed, and soya.

7. The method of claim 5, wherein said seeds are oats.

8. The method of claim 1, wherein said proteinaceous, material is derived from grinding a starting protein source and extracting lipids from the resulting ground material with an organic solvent.

9. The method of claim 1, wherein said proteinaceous material has a protein concentration of from about 10% to 50%.

10. The method of claim 9, wherein said protein concentration is from about 20% to 30%.

11. The method of claim 1, wherein said proteinaceous material has an average particle size of from about 1 $\mu$m to 600 $\mu$m.

12. The method of claim 11, wherein said particle size is from about 100 $\mu$m to 300 $\mu$m.

13. The method of claim 1, wherein said proteinaceous material is derived from oats and has a protein concentration of from about 20% to 30% and an average particle size of from about 100 $\mu$m to 300 $\mu$m.

14. The method of claims 1 or 12, wherein said proteinaceous material is buoyant and floats freely on the oil on top of water.

15. The method of claims 1 or 13, wherein said proteinaceous material is formed into a pellet.

16. The method of claim 15, wherein said pellet is formed through contacting the proteinaceous material with a liquid and evaporating the liquid.

17. The method of claim 15, wherein said pellet is formed through extruding the proteinaceous material with a binder.

18. The method of claims 16 or 17, wherein said binder is selected from the group consisting of magnesium salts, zinc salts, and calcium salts.

19. The method of claim 15, wherein said pellet is coated with a material that is insoluble in water but soluble in oil.

20. The method of claims 1 or 15, wherein said proteinaceous material is mixed with an active culture of a bacterium that biodegrades oil.

21. The method of claim 3, wherein the proteinaceous material is derived from oats from which lipids have been removed.

22. The method of claim 21, wherein said proteinaceous material has a protein concentration of from about 10% to 50%.

23. The method of claim 22, wherein said protein concentration is from about 20% to 30%.

24. The method of claim 21, wherein said proteinaceous material has an average particle size of from about 1 $\mu$m to 600 $\mu$m.

25. The method of claim 24, wherein said particle size is from about 100 $\mu$m to 300 $\mu$m.

26. The method of claim 21, wherein said proteinaceous material is derived from oats and has a protein concentration of from about 20% to 30% and an average particle size of from about 100 $\mu$m to 300 $\mu$m.

* * * * *